(12) United States Patent
Yoshii et al.

(10) Patent No.: US 12,232,741 B2
(45) Date of Patent: Feb. 25, 2025

(54) MEDICAL DEVICE, APPLICATOR, AND CLIP UNIT

(71) Applicant: OLYMPUS CORPORATION, Tokyo (JP)

(72) Inventors: Toshihiro Yoshii, Hirosaki (JP); Tomohiro Tsuji, Hino (JP); Toshinori Tamura, Hirosaki (JP)

(73) Assignee: OLYMPUS CORPORATION, Tokyo (JP)

( * ) Notice: Subject to any disclaimer, the term of this patent is extended or adjusted under 35 U.S.C. 154(b) by 699 days.

(21) Appl. No.: 17/342,976

(22) Filed: Jun. 9, 2021

(65) Prior Publication Data

US 2021/0290245 A1 Sep. 23, 2021

Related U.S. Application Data

(63) Continuation of application No. PCT/JP2019/048489, filed on Dec. 11, 2019.

(30) Foreign Application Priority Data

Dec. 11, 2018 (WO) .................. PCT/JP2018/045450

(51) Int. Cl.
*A61B 17/128* (2006.01)
*A61B 17/122* (2006.01)
*A61B 17/3205* (2006.01)

(52) U.S. Cl.
CPC ...... *A61B 17/1285* (2013.01); *A61B 17/1227* (2013.01); *A61B 17/32056* (2013.01)

(58) Field of Classification Search
CPC ............ A61B 17/1285; A61B 17/1227; A61B 17/122; A61B 2017/0034; A61B 17/1222;
(Continued)

(56) References Cited

U.S. PATENT DOCUMENTS

| 2002/0045909 A1 | 4/2002 | Kimura et al. |
| 2011/0245855 A1 | 10/2011 | Matsuoka et al. |
| 2018/0085122 A1* | 3/2018 | Ryan .................. A61B 17/1227 |

FOREIGN PATENT DOCUMENTS

| JP | 2002-191609 A | 7/2002 |
| JP | 2009-125548 A | 6/2009 |

(Continued)

OTHER PUBLICATIONS

Feb. 25, 2020 Search Report issued in International Patent Application No. PCT/JP2019/048489.

*Primary Examiner* — Kathleen S Holwerda
*Assistant Examiner* — Daniel Icet
(74) *Attorney, Agent, or Firm* — Oliff PLC

(57) ABSTRACT

A medical device, a clip unit, and a method for indwelling a clip unit. The medical device includes a treatment portion, an operation wire that can operate the treatment portion, and a link that can releasably connect the treatment portion and the operation wire. The link includes a hook that includes first and second deformation portions, and a base that can be releasably coupled to the hook. The first deformation portion is capable of being deformed by movement of the operation wire, and the second deformation portion is capable of being deformed by further movement of the operation portion after the first deformation portion is deformed.

15 Claims, 27 Drawing Sheets

(58) Field of Classification Search
CPC ............... A61B 17/128; A61B 17/10; A61B 2017/1205; A61B 2017/12054; A61B 17/32056; A61B 17/1225; A61B 17/064; A61B 2017/00296; A61B 2017/0649; A61B 2017/2931; A61B 2017/294
See application file for complete search history.

(56) References Cited

FOREIGN PATENT DOCUMENTS

| | | |
|---|---|---|
| JP | 2011-206488 A | 10/2011 |
| JP | 5750620 B2 | 7/2015 |

* cited by examiner

FIG. 28
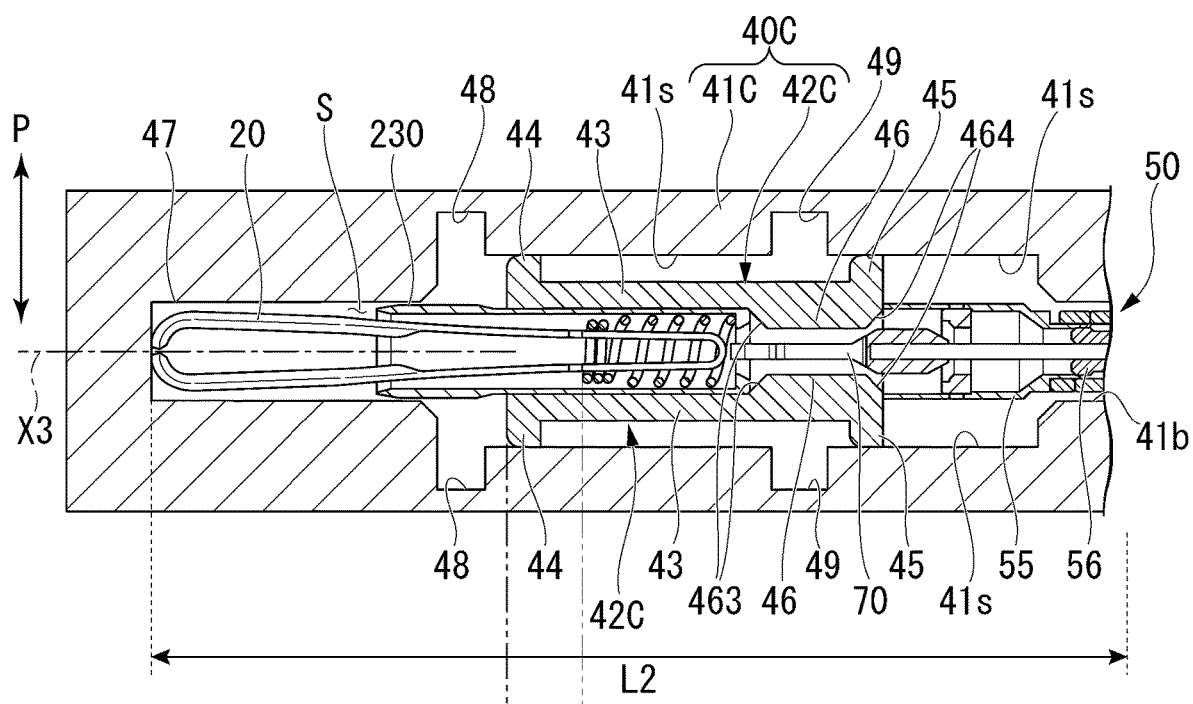
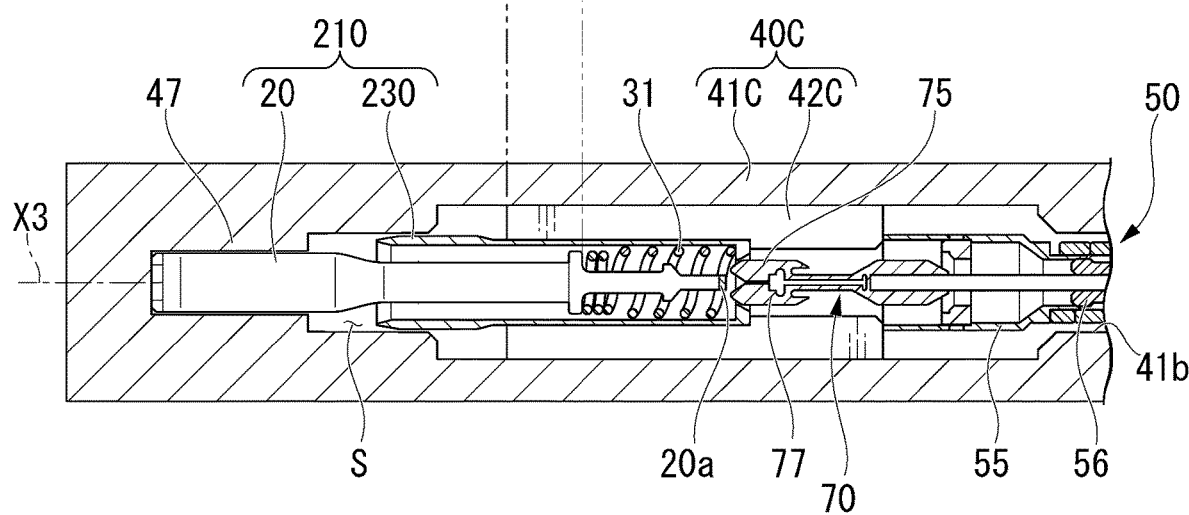

FIG. 30
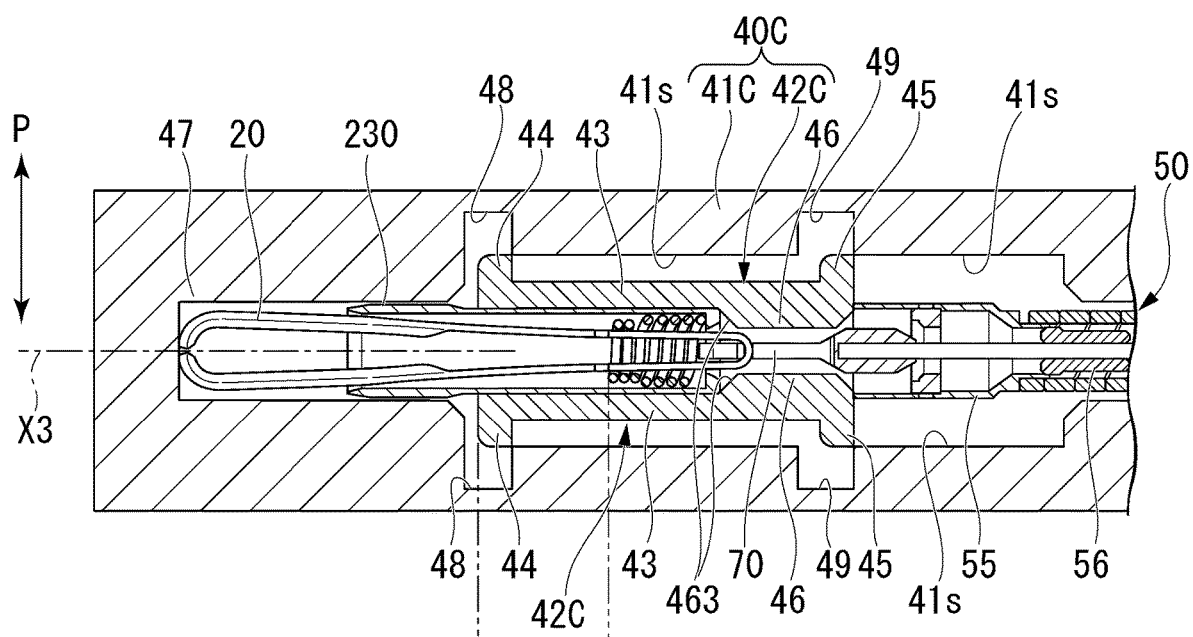
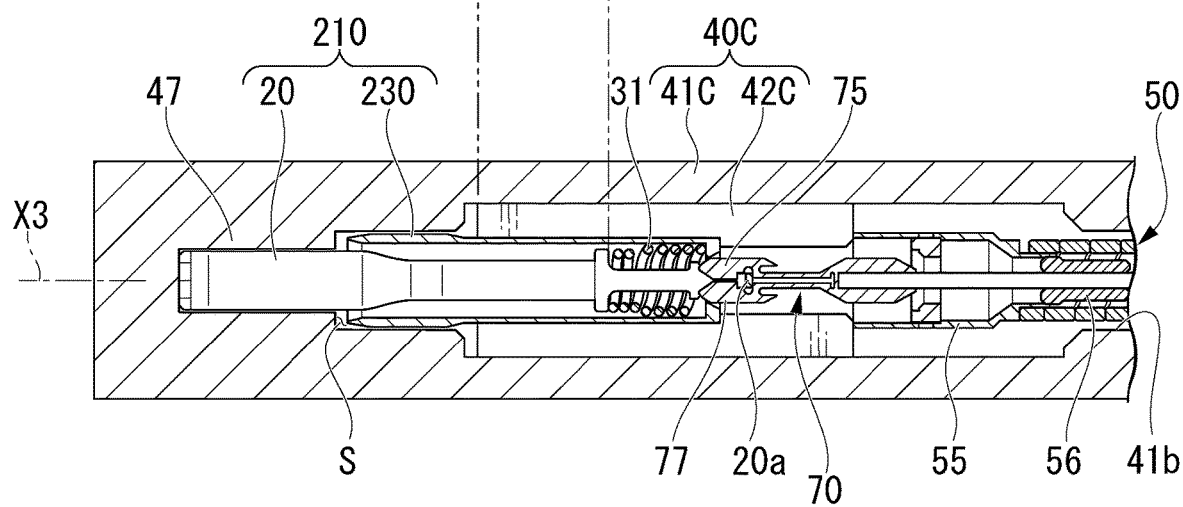

FIG. 32
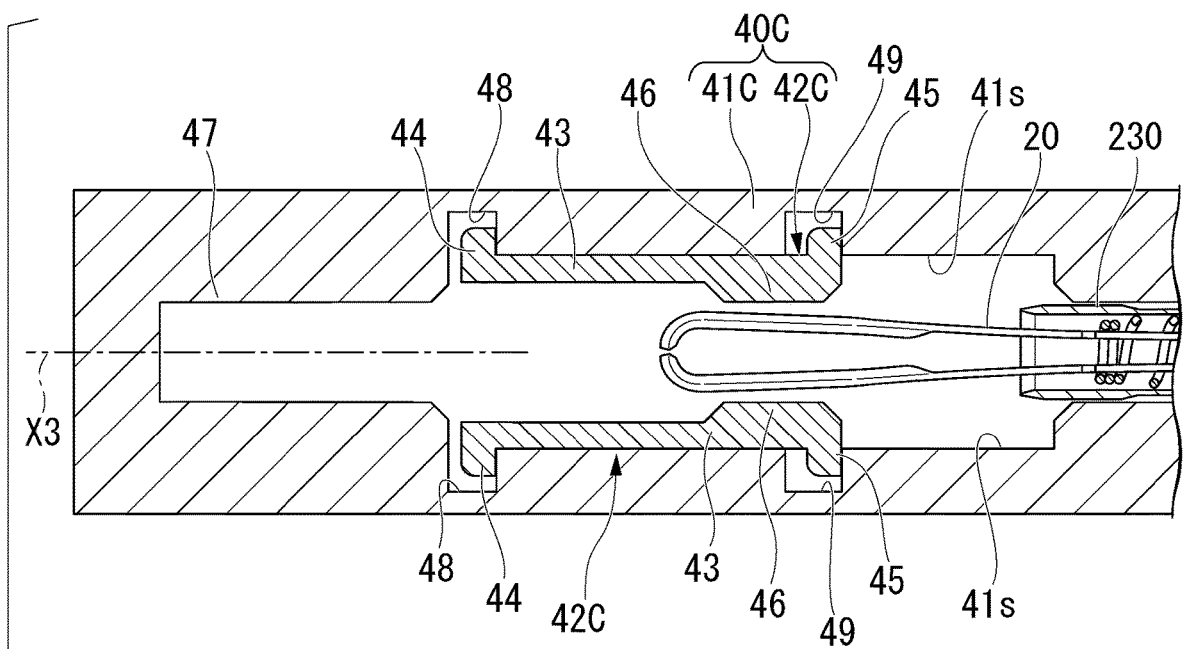
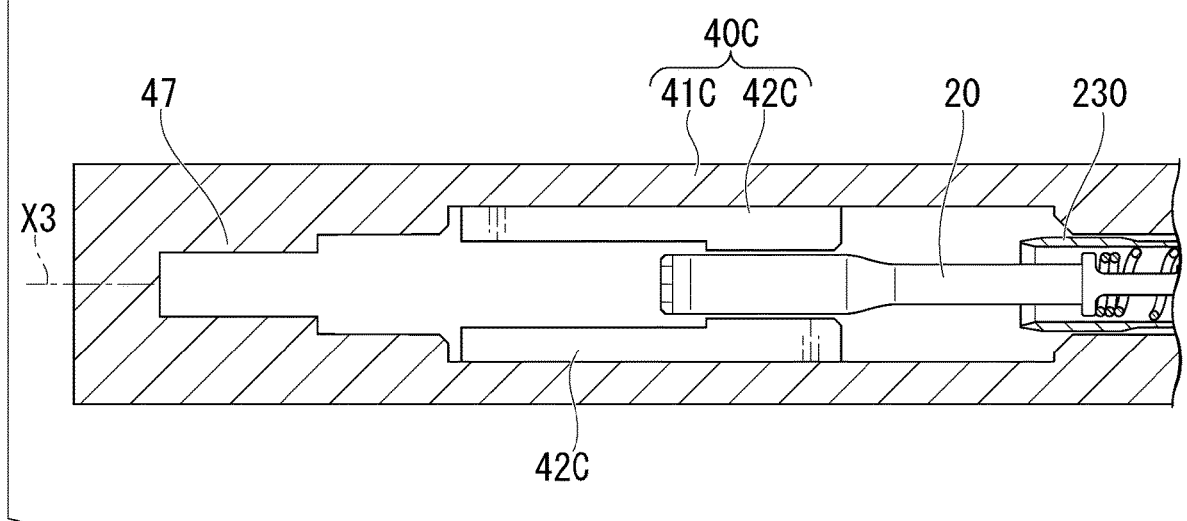

MEDICAL DEVICE, APPLICATOR, AND CLIP UNIT

This application is a continuation application of PCT International Application No. PCT/JP2019/048489, filed on Dec. 11, 2019, whose priority is claimed on PCT International Application No. PCT/JP2018/045450, filed on Dec. 11, 2018. The content of both PCT International Applications are incorporated herein by reference.

TECHNICAL FIELD

The present disclosure relates to a medical device, particularly a ligation device and an applicator and a clip unit configuring the ligation device.

BACKGROUND

Conventionally, a ligation using a clip unit is known as a treatment using an endoscope. The clip unit has a pair of arms. When the pair of arms are retracted by a predetermined amount in a state in which the pair of arms grasp the tissue, the pair of arms are locked in a state in which the tissue is tightly bound.

The clip unit is introduced to the body in a state of being attached to an applicator. In order to indwell the clip unit in the body in with the tissue to be ligated, it is necessary to cut off the pair of arms from the application after being locked.

Several aspects to release the connection of the applicator and the clip unit are known. For example, there are an aspect of fracturing a member connecting the applicator and the clip unit, an aspect of deforming the member rather than fracturing the member, and an aspect of releasing the connection by rotating the member.

The aspect of releasing the connection by deformation is superior than the aspect of releasing the connection by fracturing the member since there is no fragment generated. The aspect of releasing the connection by deformation is superior than the aspect of releasing the connection by rotation since the connection may be released by only a retraction operation of an operation transmission member connected to the member.

SUMMARY

According to an aspect of the present disclosure, a medical device includes a treatment portion; an operation wire configured to operate the treatment portion; and a link configured to releasably connect the treatment portion to the operation wire. The link includes a hook; a first deformation portion disposed in the hook and configured to be deformed by movement of the operation wire; a second deformation portion disposed in the hook and configured to be deformed by further movement of the operation wire after the first deformation portion is deformed; and a base capable of being coupled to the hook.

The present disclosure also relates to an applicator to which a treatment portion including a base is attached. The applicator includes an operation wire for operating the treatment portion; and a hook that is connected to the operation wire and engageable with the base. The hook includes a first deformation portion and a second deformation portion that are configured to be deformed due to a force received from the operation wire. In a connection state in which the hook and the base are connected to each other, the first deformation portion is separated from a base line, and the base line is defined as a line running through the second deformation portion and a contact portion of the hook and the base.

The present disclosure also relates to a clip unit attached to an applicator including an operation wire with a base provided at a distal end portion thereof. The clip unit includes a hook that is engageable to the base. The hook includes a first deformation portion and a second deformation portion that are configured to be deformed due to a force received from the operation wire. In a connection state in which the hook and the base are connected to each other, the first deformation portion is separated from a base line, and the base line is defined as a line passing through the second deformation portion and a contact portion of the hook and the base.

The present disclosure also relates to a method for indwelling a clip unit. The method includes retracting an operation wire for operating the clip unit to cause a first deformation portion to be deformed. The first deformation portion is comprised by a hook that connects the clip unit and the operation wire. Then, in a state in which the first deformation portion is deformed, the method includes further pulling the operation wire to cause a second deformation portion different from the first deformation portion in the hook to be deformed such that the connection between the clip unit and the operation wire due to the hook is released.

BRIEF DESCRIPTION OF DRAWINGS

FIG. 28 is a partial cross-sectional view of a connection portion during a connection step using a cartridge having another modification of a fastener.

FIG. 30 is a partial cross-sectional view of a connection portion during a connection step using a cartridge having a further modification of a fastener.

FIG. 32 is a partial cross-sectional view of a connection portion during a connection step using a cartridge having a further modification of a fastener.

DESCRIPTION OF EMBODIMENTS

An exemplary embodiment of the present disclosure will be described with reference to FIGS. 1 to 15.

Figure 1:
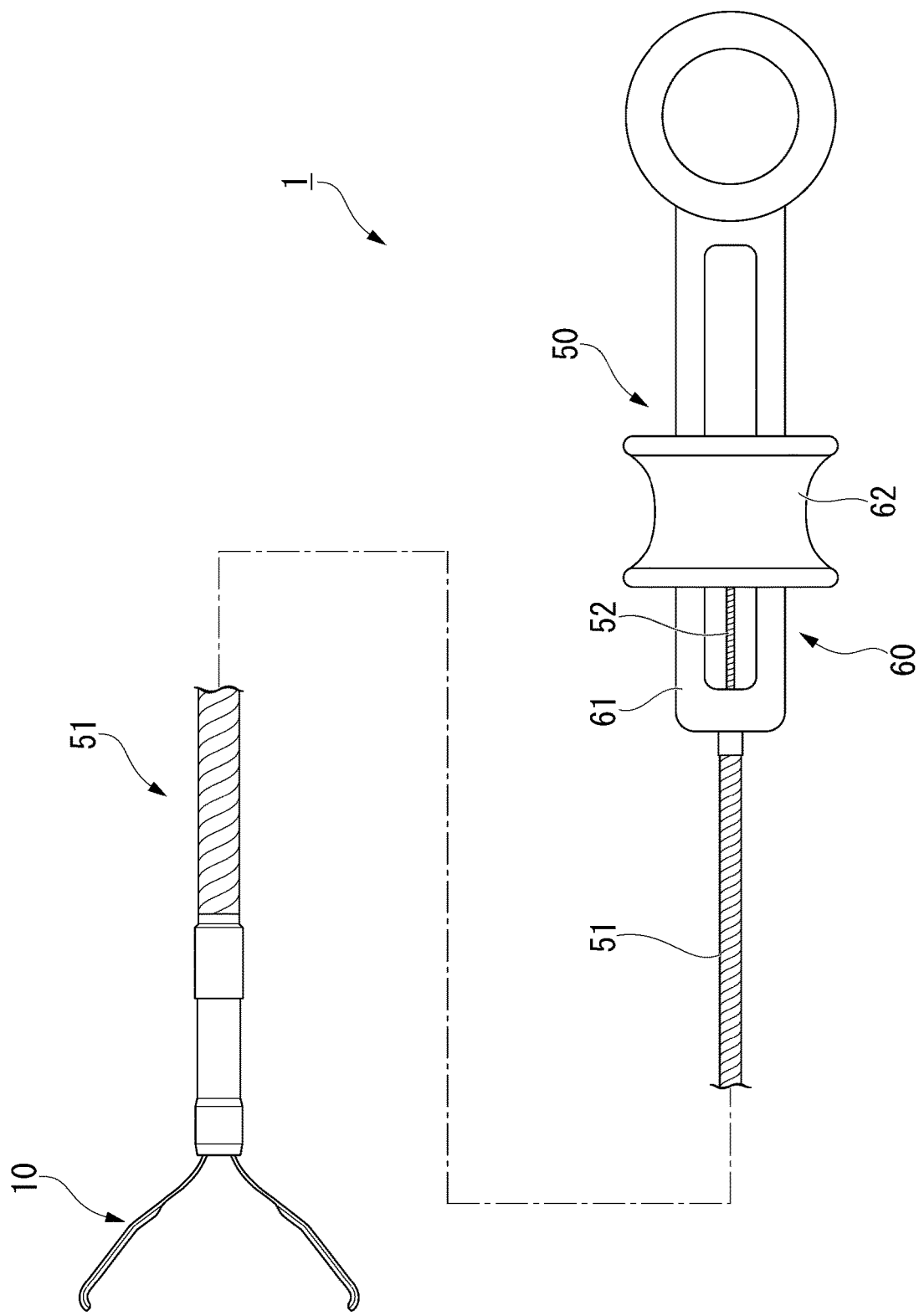
FIG. 1 is a view showing an overall configuration of a ligation device according to an exemplary embodiment of the present disclosure.

FIG. 1 is a view showing an appearance of a ligation device 1 as a medical device according to the present embodiment. The ligation device 1 includes a clip unit (treatment portion) 10 indwelled inside the body, and an applicator 50 configured to operate the clip unit 10. The clip unit 10 is attached to a tip end (distal end) of the applicator 50.

Figure 2:
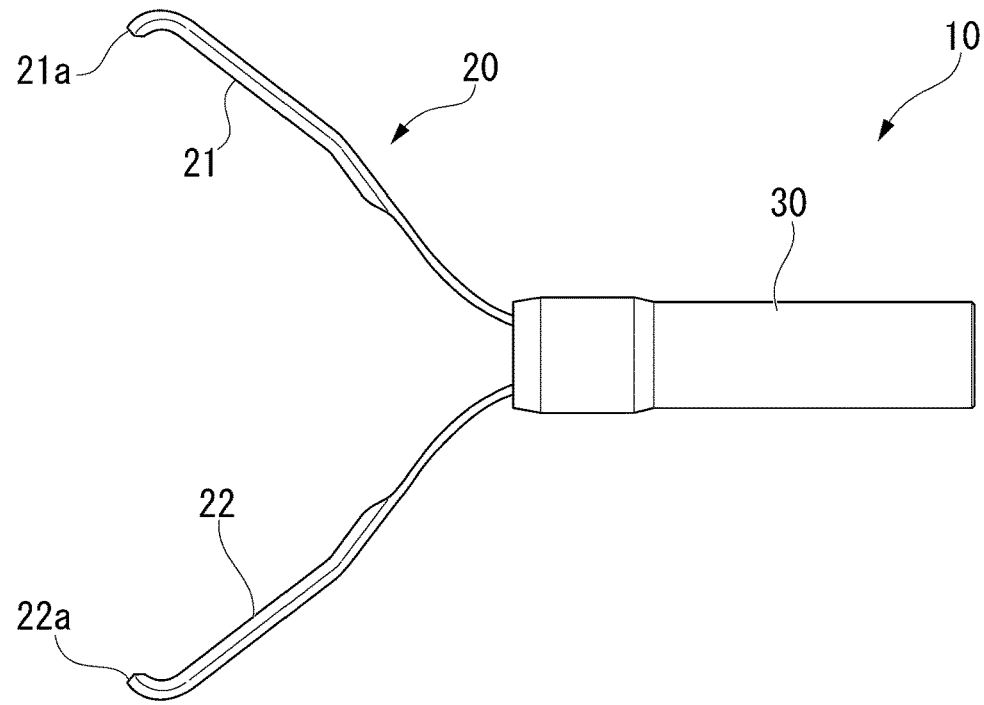
FIG. 2 is a view showing a clip unit of the present ligation device.
Figure 3:
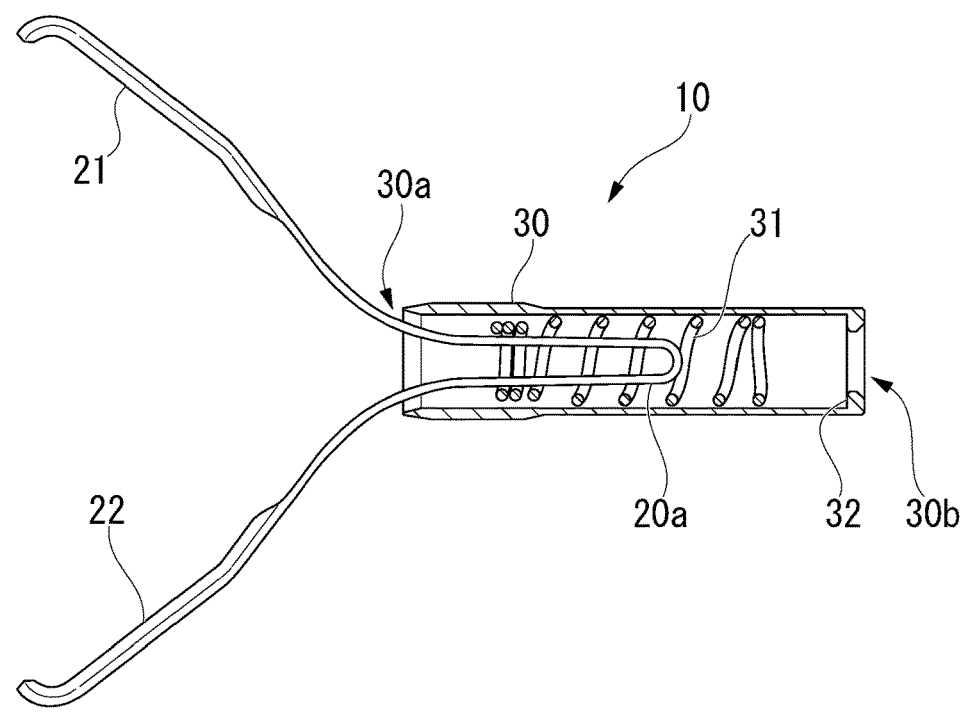
FIG. 3 is a cross-sectional view of the clip unit.

FIG. 2 is a view showing an appearance of the clip unit 10. FIG. 3 is a cross-sectional view of the clip unit 10. As shown in FIG. 2, the clip unit 10 includes an arm portion 20 and a pressing tube (holding member) 30 in which part of the arm portion 20 is accommodated.

The arm portion 20 has a pair of arms as a first arm 21 and a second arm 22. The first arm 21 and the second arm 22 have claws 21a and 22a at distal ends thereof respectively. As shown in FIG. 3, the first arm 21 and the second arm 22 are connected to each other at a proximal end portion (base) 20a of the arm portion 20. The proximal end portion 20a is formed in a U shape.

The arm portion 20 is made of metal including alloy. Examples of the material of the arm portion 20 include stainless steel, cobalt chrome alloy, nickel titanium alloy and the like.

The first arm 21 and the second arm 22 are expanded in an initial state shown in FIG. 2. When the first arm 21 and the second arm 22 approach each other from the initial state, a biasing force for restoring to the initial state is generated due to an elastic force of the material.

The pressing tube 30 is a tubular member formed of metal, resin, or the like. As shown in FIG. 3, the proximal end portion 20a of the arm portion 20 is accommodated in the pressing tube 30. The distal end portion of the arm portion 20 protrudes from the distal end opening 30a of the pressing tube. The proximal end opening 30b of the pressing tube 30 is smaller than the distal end opening 30a.

Figure 4:
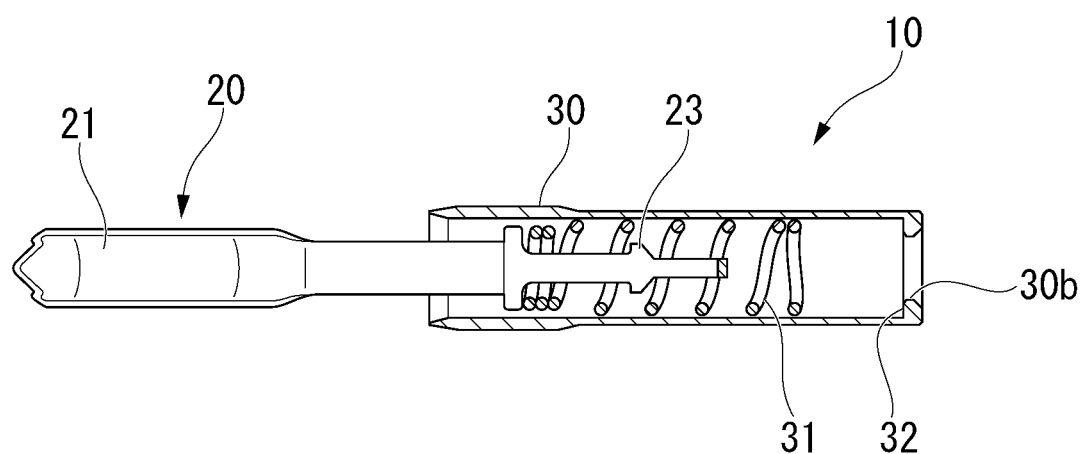
FIG. 4 is a cross-sectional view of the clip unit showing a cross section along a different direction from that shown in FIG. 3.

FIG. 4 is a view of the inside of the pressing tube 30 viewed from a direction different from that in FIG. 3. As shown in FIG. 4, a locking portion 23 is provided at an intermediate portion of each arm of the arm portion 20, and a width of each arms 21, 22 at the locking portion 23 is large (only the first arm 21 is visible in FIG. 4). Each locking portion 23 is capable of passing through the proximal end opening 30b when the first arm 21 and the second arm 22 approach each other. When the first arm 21 and the second arm 22 are separated from each other after passing through the proximal end opening 30b, the locking portion 23 is impossible to pass through the proximal end opening 30b. As a result, the arm portion 20 is locked with the pair of arms closed.

A coil spring 31 is arranged inside the pressing tube 30. The distal end of the coil spring 31 may contact the proximal surfaces of the first arm 21 and the second arm 22. The proximal end of the coil spring 31 may come into contact with the proximal end surface 32 of the pressing tube 30 having the proximal end opening 30b.

The basic configurations of the arm portion 20 and the pressing tube 30 described above are known, for example, as disclosed in PCT International Publication No. 2014/181676.

As shown in FIG. 1, the applicator 50 includes an elongated insertion portion 51, an operation wire (power transmission member) 52 inserted through the insertion portion 51, and an operation portion 60 connected to the insertion portion 51.

As the insertion portion 51, for example, a sheath formed of a coil may be used.

The operation portion 60 has a main body 61 connected to the insertion unit 51, and a slider 62 slidably attached to the main body 61.

For example, a stranded wire made of a metal element wire may be used as the operation wire 52. A proximal end portion of the operation wire 52 is connected to the slider 62. By moving the slider 62 with respect to the main body 61, the operation wire 52 may be advanced and retracted in the insertion portion 51.

Figure 5:
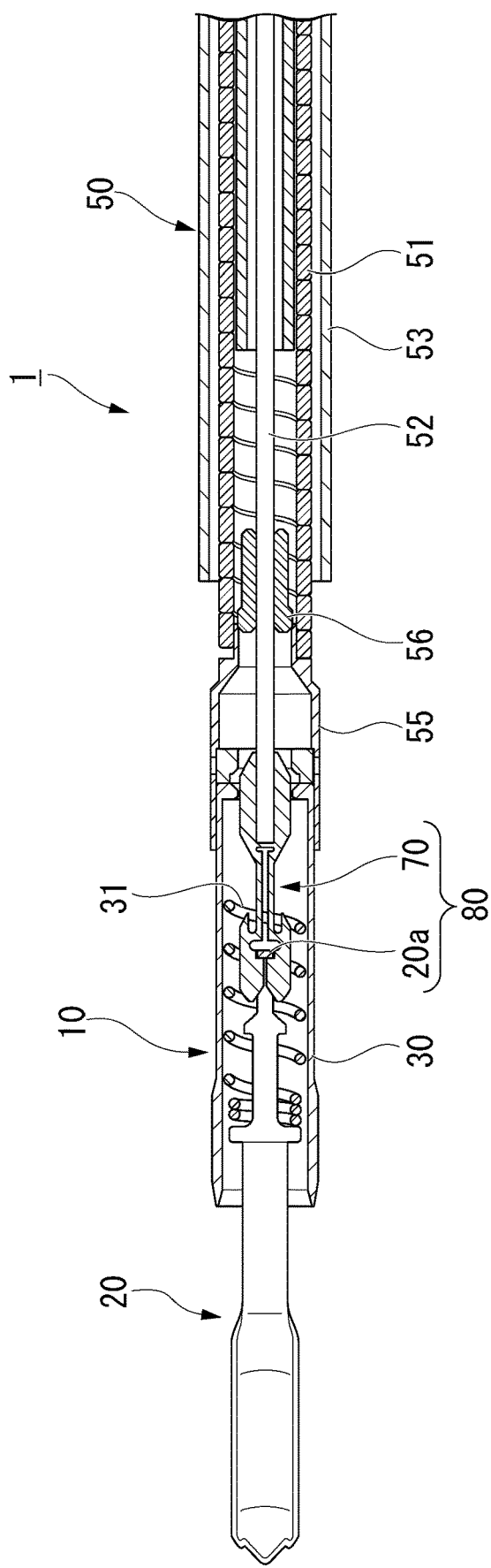
FIG. 5 is an enlarged cross-sectional view showing a clip attachment portion in the ligation device.

FIG. 5 is an enlarged cross-sectional view of the distal end portion of the applicator 50 to which the clip unit 10 is attached.

A hook 70 that engages with the clip unit 10 is fixed to the distal end of the operation wire 52. As shown in FIG. 5, the distal end portion of the operation wire 52 enters the pressing tube 30, and the hook 70 and the proximal end portion 20a of the arm portion 20 are engaged with each other. An outer dimension of the hook 70 is slightly smaller than an inner diameter of the coil spring 31.

In the following description, the proximal end portion 20a may be referred to as the "a base 20a". The hook 70 and the base 20a configure a link 80 that connects the applicator 50 and the clip unit 10.

Figure 6:
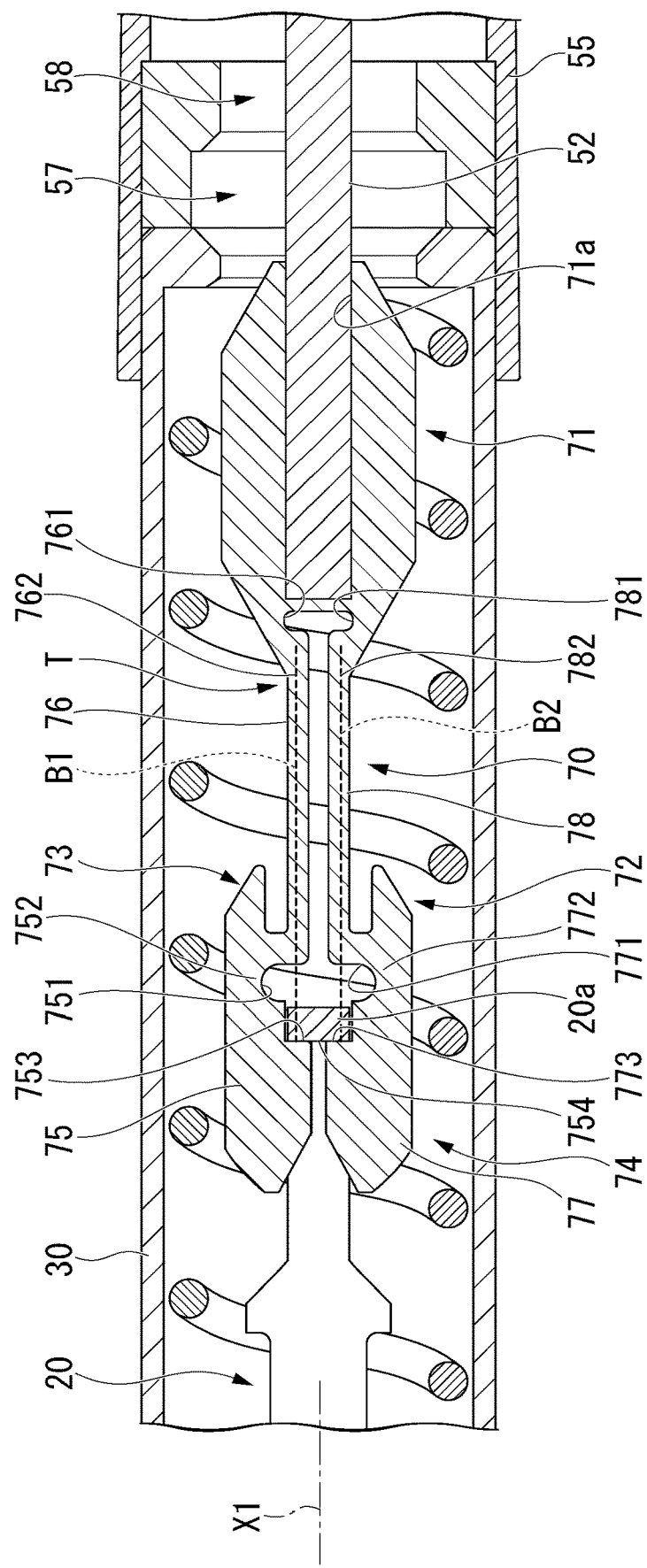
FIG. 6 is an enlarged view of a hook.

FIG. 6 is an enlarged view of the hook 70. The hook 70 has a rear portion 71 connected to the operation wire 52 and a front portion 72 engaging with the base 20a.

The rear portion 71 is formed in a spindle shape that gradually shrinks toward both ends in the front-rear direction, and has a bottomed hole 71a opening at the rear end. The distal end portion of the operation wire 52 enters the hole 71a. The operation wire 52 and the hook 70 are connected, for example, by brazing or the like. According to the present embodiment, the hook 70 and the operation wire 52 are connected while maintaining a coaxial state.

The front portion 72 has a pair of engagement arms 73 and 74. The engagement arm 73 has a claw portion 75 that contacts the base 20a and a plate-shaped portion 76 that connects the claw portion 75 and the rear portion 71. Similar to the engaging arm 73, the engaging arm 74 has a claw portion 77 and a plate-shaped portion 78 with the same shapes as those of the engaging arm 73. The engagement arms 73 and 74 are provided at positions symmetrical with respect to a central axis X1 of the hook 70.

Hereinafter, the shape and structure of the engagement arm 73 will be described in detail, and the same description is applicable to the engagement arm 74.

A notch 751 is formed on an inner surface of the claw portion 75 more distal than a connection portion between the plate-shaped portion 76 and the claw portion 75. In the claw portion 75, a region where the notch 751 is formed has a reduced bending rigidity since there is less configuration material, and the region functions as a first deformation portion 752. A three-dimensional shape of the notch 751 is not particularly limited.

A locking surface (hook surface) 753 that is locked to the distal surface (base surface) 754 of the base 20a is formed more distal than the first deformation portion 752. The locking surface 753 extends in a direction intersecting the central axis X1 in the cross section shown in FIG. 6. A portion more distal than the locking surface 753 is formed in a tapered shape that gradually shrinks toward the distal end in the cross section shown in FIG. 6.

The plate-shaped portion 76 extends parallel or substantially parallel to the central axis X1. Therefore, according to the present embodiment, the plate-shaped portion 76 extends parallelly or substantially parallelly to the operation wire 52. A notch 761 is formed more proximal than a connection portion T between the plate portion 76 and the rear portion 71. The plate-shaped portion 76 is formed to be easily deformed since the configuration material thereof is less than that of the front portion 72 and the rear portion 71. Particularly, the plate-shaped portion 76 near the connection portion T is the farthest from the engaging portion between the hook 70 and the base 20a, and a change of thickness in the connection portion T is large such that it is easy for stress to be concentrated thereto. As a result, the plate-shaped portion 76 near the connection site T functions as a second deformation portion 762. A bending rigidity of the second deformation portion 762 is smaller than the bending rigidity of the first deformation portion 752.

The engagement arms 73 and 74 sandwich the base 20a from a direction orthogonal to an open-close direction of the arm portion 20. In the state in which the hook 70 and the base 20a are engaged with each other, the hook surface 753 and the base surface 754 are in contact with each other more distal than the first deformation portion 752. Accordingly, the first deformation portion 752 is closer to the hook surface 753 than the second deformation portion 762. Furthermore, in the engagement arm 73, the first deformation portion 752 is at a position separated from a base line B1 defined as a line connecting the hook surface 753 and the second deformation portion 762. According to the present embodiment, the base line B1 is parallel to the central axis line X1.

Similar to the engagement arm 73, the engagement arm 74 has a notch 771, a first deformation portion 772, a hook surface 773, a notch 781, and a second deformation portion 782. In the engaging arm 74, the first deformation portion 772 is at a position separated from a base line B2 defined as a line connecting the hook surface 773 and the second deformation portion 782. According to the present embodiment, the base line B2 is parallel to the central axis line X1.

As shown in FIG. 5, a rigid guide pipe 55 is attached to the distal end of the insertion portion 51. An inner diameter of the distal end side region of the guide pipe 55 is larger than the outer diameter of the pressing pipe 30, and the pressing pipe 30 is capable of entering the guide pipe 55. A stopper 56 is attached to the operation wire 52. Since a shape and a size of the stopper 56 are set such that the stopper 56 is impossible to enter the guide pipe 55, when the stopper 56 comes into contact with the proximal end of the guide pipe 55, the operation wire 52 is impossible to advance any further.

An operation when the ligation device 1 configured as described above is used will be described. The ligation device 1 is introduced into the body via a channel of an endoscope. When inserting the ligation device 1 into the endoscope, the user retracts the slider 62 by a predetermined amount to insert the ligature device 1 with the arm portion 20 closed and in an unlocked state. The clip unit 10 with the arm portion 20 closed and the distal end portion of the insertion portion 51 may be inserted into the endoscope while being accommodated in the outer sheath 53.

When the ligation device 1 is protruded from the channel opening at the distal end of the endoscope, and then the pulling force with respect to the slider is reduced or the sheath is retracted, the arm portion 20 advances toward the pressing tube 30 due to its own elastic restoring force and the elastic restoring force of the coil spring 31. As a result, the pair of arms 21, 22 is in an open configuration. When the stopper 56 comes into contact with the rear end of the guide pipe 55, the arm portion 20 is impossible to advance with respect to the pressing tube 30, such that the arm portion 20 does not slip out from the pressing tube 30 and the open configuration is maintained.

When the user retracts the slider 62 with respect to the main body 61, the operation wire 52 is pulled and the arm portion 20 retracts with respect to the pressing tube 30, and as a result, the pair of arms 21, 22 enter a closed configuration. The user may ligate the tissue by positioning the tissue between the pair of arms 21, 22 and closing the pair of arms 21, 22. Until a locking operation described below is performed, the pair of arms 21 may be transitioned from the closed configuration to the open configuration again by advancing the slider 62 with respect to the main body 61. Accordingly, in the ligation device 1, until the locking operation is performed, the re-grasp of the tissue by the operation wire 52 operating the clip unit 10 may be performed.

In the guide pipe 55, a restriction member 57 configured to prevent the connection between the base 20a and the hook 70 from being unintentionally released is disposed. The restriction member 57 has a small diameter portion 58 having a slightly larger than the outer diameter of the hook 70. In order to release the engagement between the base 20a and the hook 70, the engagement arms 73 and 74 have to be separated by a certain distance or more; however, there is no sufficient space in the small diameter portion 58 for the engagement arm 73 and the engagement arm 74 to be separated from each other. As a result, the engagement between the hook 70 and the base 20a is not released until the engagement arms 73 and 74 pass through the small diameter portion 58, and the engaged state is suitably maintained.

When it is determined that the tissue located between the pair of arms 21 and 22 may be ligated, the user performs a locking operation for fixing the arm unit 20 in the closed configuration. During the locking operation, the user further retracts the slider 62 with respect to the main body 61 beyond the range where the user may grasp the tissue again. When the slider 62 retracts, the operation wire 52 is pulled and the pair of arms 21, 22 enter the pressing tube 30 in a substantially parallel state while clamping the tissue. Furthermore, the locking portions 23 provided on the pair of arms 21, 22 respectively approach each other, and the positional relationship is determined such that they may pass through the proximal end opening 30b of the pressing tube 30.

The pair of locking portions 23 that have moved to the outside of the pressing tube 30 after passing through the proximal end opening 30b are separated again since the force received from the operation wire 52 weakens, and the pair of locking portions 23 have a positional relationship in which they cannot pass through the proximal end opening 30b. As a result, the pair of locking portions 23 are in contact with an edge of the proximal end opening 30b so as to prevent the arm portion 20 from protruding from the pressing tube 30, and the arm portion 20 is locked to maintain the closed configuration.

During the process of the locking operation, the base 20a and the hook 70 move to the outside of the pressing tube 30 through the proximal end opening 30b; however, the engagement state between the base 20a and the hook 70 is suitably maintained.

When the user further retracts the slider 62 after the arm portion 20 is locked, the engagement between the base 20a and the hook 70 is released, and the clip unit 10 is separated from the applicator 50. Hereinafter, the operation of the hook 70 during the locking operation will be described in detail.

When the slider 62 is retracted, the operation wire 52 is pulled, and the traction force F applies on the hook 70. In a state immediately after the hook 70 moves to the outside of the pressing tube 30, the plate-shaped portions 76, 78 (not shown) are parallel or substantially parallel to the central axis X1 as shown in FIG. 6. Accordingly, there is no moment generated for rotating the plate-shaped portions 76, 78 due to the traction force F. Therefore, the engagement arms 73 and 74 do not rotate around the second deformation portion at this time.

Figure 7:
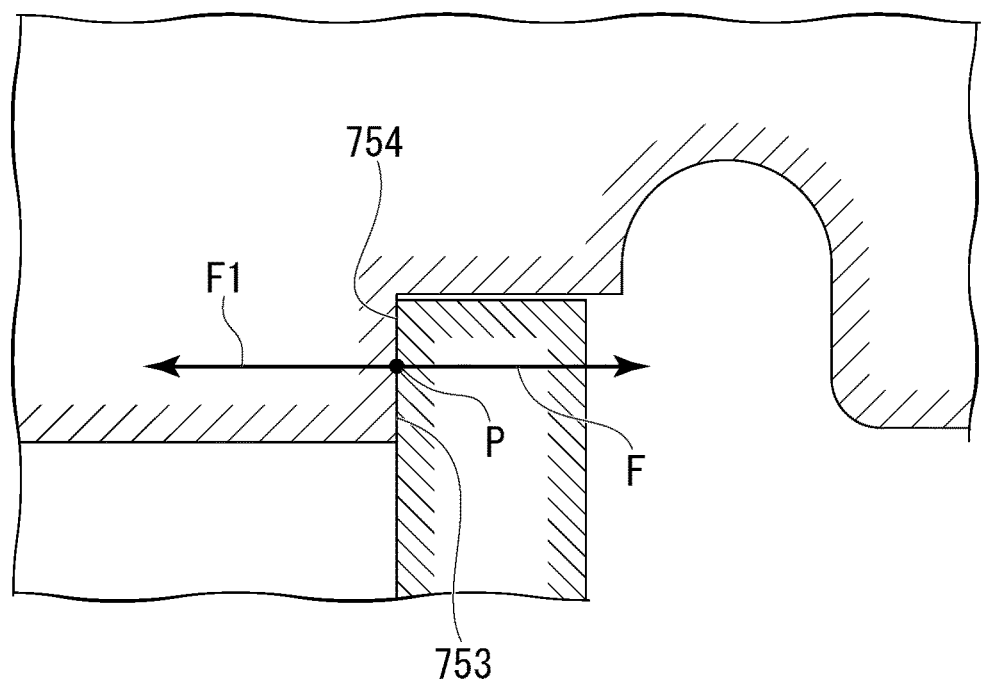
FIG. 7 is a view showing a force applied to a hook surface and a locking surface.

FIG. 7 is a schematic enlarged view of the hook surface 753 and the base surface 754. The traction force F is transmitted through the plate-shaped portion 76 and firstly applies on the contact portion P between the hook surface 753 and the base surface 754 (that is, the contact portion between the hook 70 and the base 20a in the connection state) so as to generate a reaction force F1 on the hook surface 753.

Figure 9:
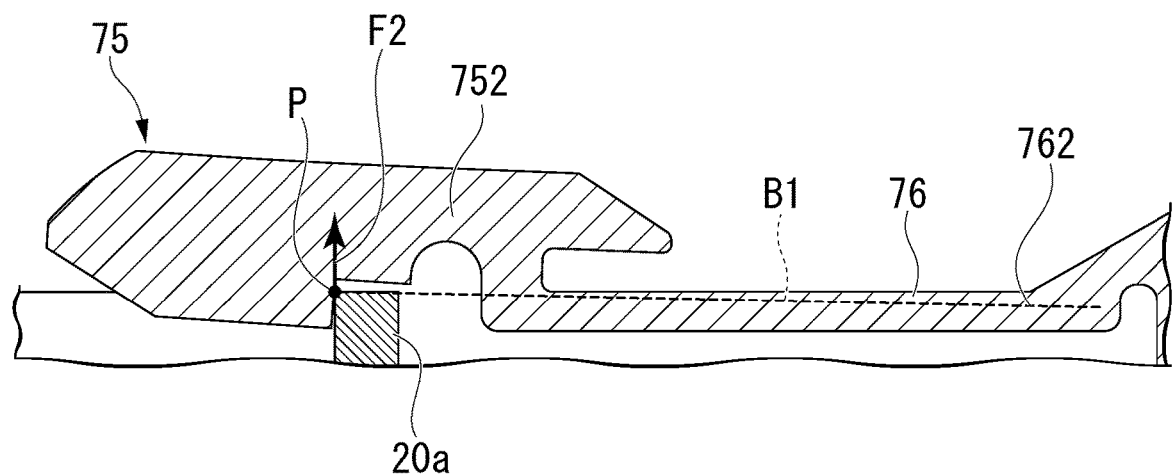
FIG. 9 is a view showing a first engagement arm and a base.
Figure 10:
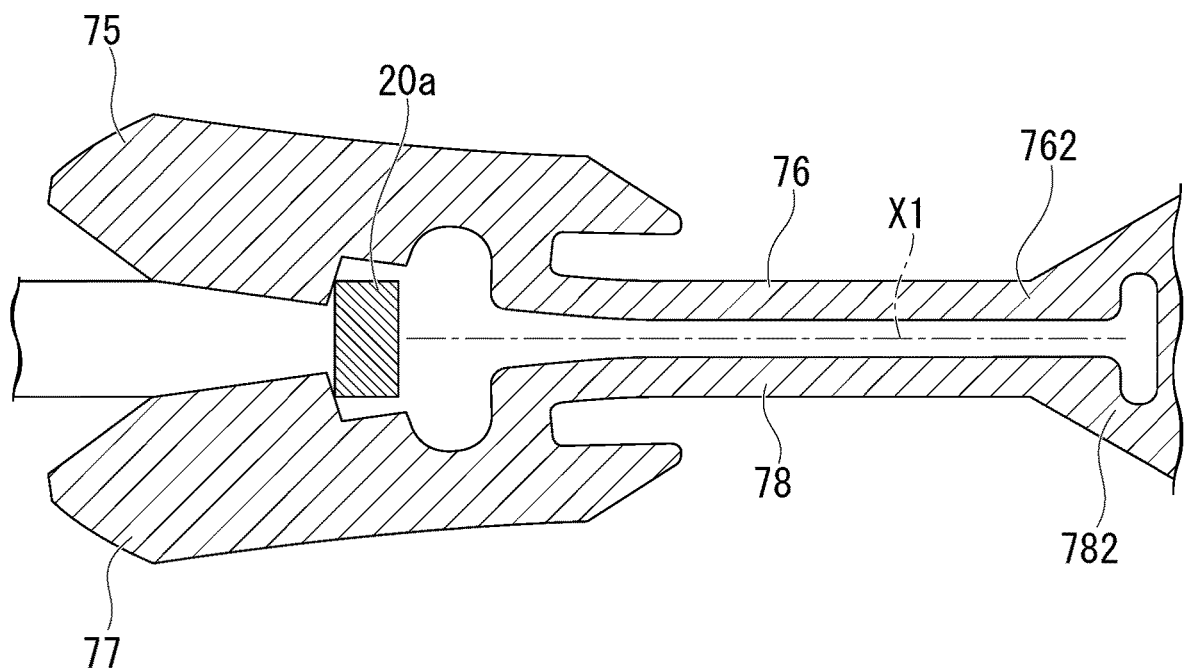
FIG. 10 is a view showing a process for releasing the connection of the hook and the base.

As shown in FIG. 9, since the first deformation portion 752 is located separated from the base line B1 defined as a line passing through the contact portion P and the second deformation portion 762, the reaction force F1 is applied to the claw portion 75 as a moment. As a result, the distal end portion of the claw portion 75 is deformed so as to rotate around the first deformation portion 752. Although it is not shown in figures, a force similar to the reaction force F1 also applies on the claw 77. As a result, the distal end portion of the claw portion 77 is deformed so as to rotate around the first deformation portion 772.

Since the base lines B1 and B2 are parallel to the central axis line X1, the second deformation portion 762 and the contact portion P, and the second deformation portion 782 and the contact portion P are arranged parallel to the central axis line X1. Therefore, the reaction force F1 does not apply on the second deformable portions 762, 782 as a moment.

Figure 8:
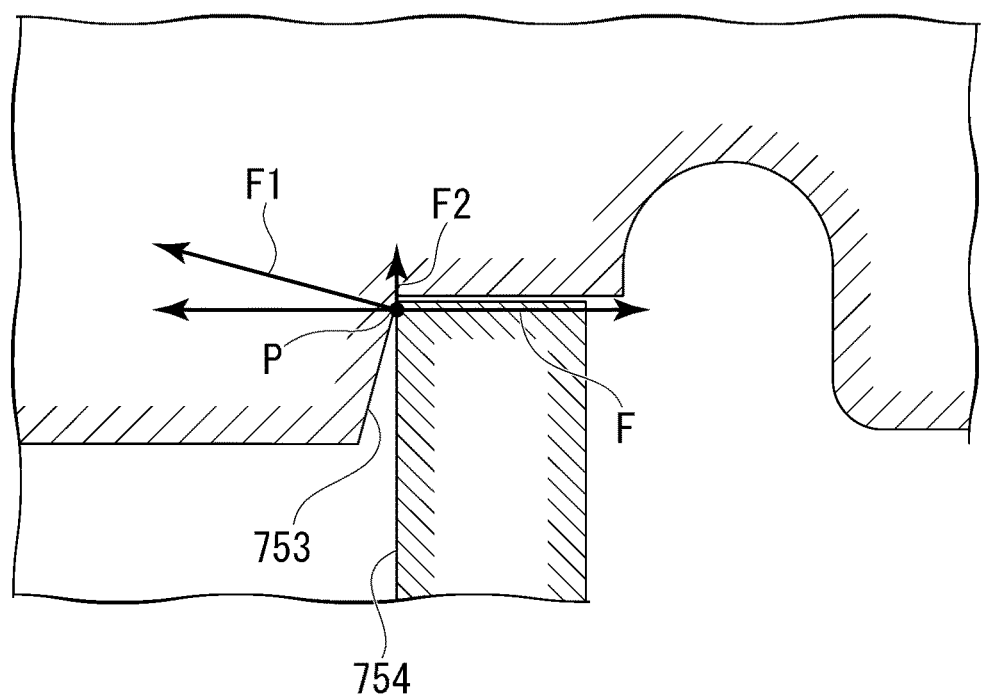
FIG. 8 is a view showing the force applied to the hook surface and the locking surface in a state after that shown in FIG. 7.

As shown in FIG. 8, when the hook surface 753 is tilted with respect to the base surface 754 as a result of the claw portion 75 deforming around the first deformation portion 752 as a center, a component force F2 of the reaction force F1 is generated in a direction from the central axis X1 toward the outside of the pressing tube 30 in the radial direction.

Figure 11:
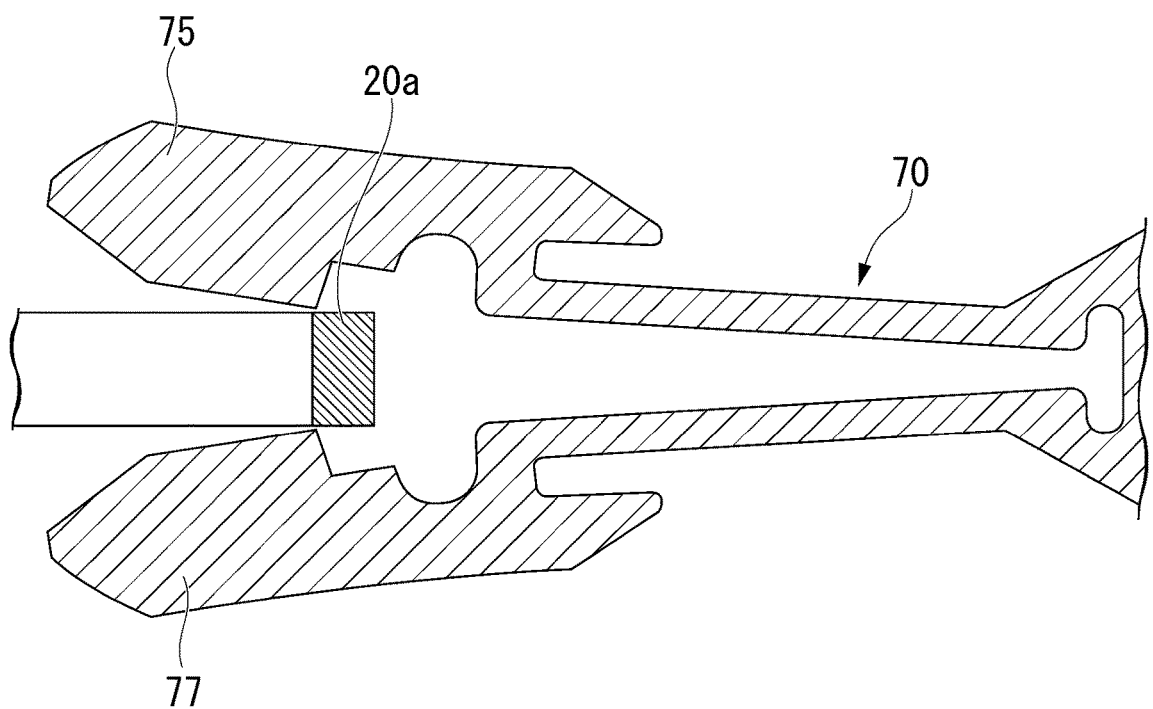
FIG. 11 is a view showing a state in which the connection of the hook and the base are released.

The component force F2 applies in the direction of separating the engagement arm 73 from the base 20a. That is, the component force F2 applies as a moment on the second deformation portions 762, 782. Due to the moment, the plate-shaped portions 76, 78 are caused to rotate around the second deformation portions 762, 782, respectively, such that the distal ends thereof are separated from each other. As a result, as shown in FIG. 11, the claw portion 75 and the claw portion 77 are largely separated from each other, and the engagement between the hook 70 and the base 20a is released.

In the hook 70 according to the present embodiment, until the component force F2 is generated by the rotation of the claws 75, 77 with the first deformation portion as the center, the rotation of the plate-shaped portions 76, 78 with the second deformation portion as the center does not occur regardless of the amount of the traction force F. Accordingly, if the amount of the force necessary for the rotation of the claws 75, 77 with the first deformation portion as the center is larger than the amount of the locking force in the case of clamping the hard tissue by the arm, even if the amount of the force necessary for the rotation of the plate-shaped portions 76, 78 with the second deformation portion as the center is set to be smaller than the amount of the locking force in the case of clamping the hard tissue by the arm, there is no case in which the connection of the hook 70 and the base 20a is released before the locking operation.

Since the hook 70 has the above-described configuration, by forming the second deformable portions 762 and 782 to be more easily deformed than the first deformation portions 752 and 772, the force necessary for the rotation of the plate-shaped portions 76, 78 with the second deformation portion as the center may be set to be significantly smaller than the locking force. As a result, after a force exceeding the locking force is applied to the claw portions 75, 77 after the arms are locked, the plate-shaped portions 76, 78 are rotated quickly to release the connection between the hook 70 and the base 20a.

In this manner, in the ligation device 1, it is possible to prevent the amount of operating force required for separating the clip unit 10 from the applicator 50 from becoming excessively large with respect to the amount of locking force for the arm of the clip unit 10. As a result, it is possible to achieve both goals of indwelling the clip unit 10 while clamping the hard tissue and easy operations.

According to the present embodiment, an example in which the hook surface is orthogonal to the central axis X1 in the initial state is described; however, the hook surface may not be orthogonal to the central axis X1 in the initial state.

Figure 12:
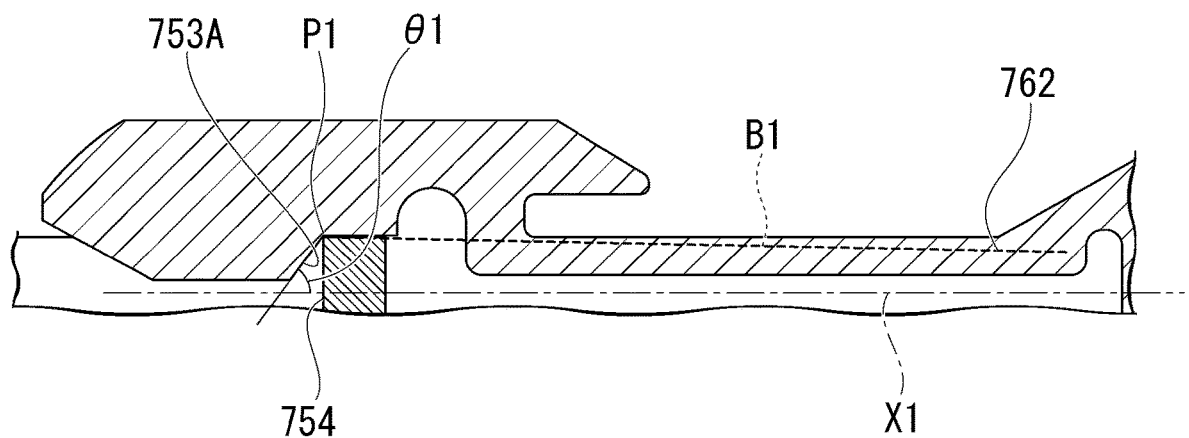
FIG. 12 is a partial enlarged view showing a modification of the hook.

In the modification shown in FIG. 12, in the initial state, the hook surface 753A is inclined to form an acute angle θ1 on the proximal end side with respect to the central axis X1. As a result, the contact portion P1 between the hook surface 753A and the base surface 754 is located farther from the central axis X1 than the contact portion P according to the above embodiment in the cross section as shown in FIG. 12. Further, the distance between the central axis X1 and the contact portion P1 is longer than the distance between the central axis X1 and the second deformation portion 762 such that the base line B1 is inclined and becomes nonparallel to the central axis X1.

According to the present modification, the timing at which the component force F2 is generated becomes earlier than the configuration including the hook surface 753 according to the above embodiment and the connection is released smoothly.

Figure 13:
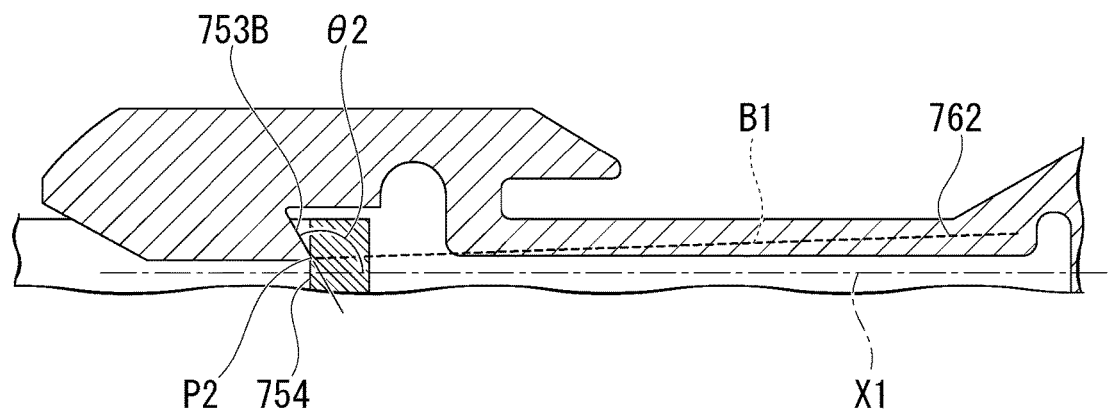
FIG. 13 is a partial enlarged view showing a modification of the hook.

According to the modification shown in FIG. 13, the hook surface 753B is inclined to form an obtuse angle θ2 on the proximal end side with respect to the central axis X1 in the initial state. As a result, the contact portion P2 between the hook surface 753B and the base surface 754 is located closer to the central axis X1 than the contact portion P in the cross section shown in FIG. 13. Further, the distance between the central axis X1 and the contact portion P1 is shorter than the distance between the central axis X1 and the second deformation portion 762, and the base line B1 is inclined and becomes nonparallel to the central axis X1. According to the present modification, the timing at which the component force F2 is generated becomes later than the configuration including the hook surface 753 according to the above embodiment (FIGS. 1-11), and the connection between the hook 70 and the base 20a may be stronger.

As described above, by changing the contact portion between the hook surface and the base surface, it is possible to variously adjust the amount and the timing for releasing the connection. The means for changing the contact portion is not limited to the means of changing the angle formed by the hook surface and the central axis X1 as described above.

Figure 14:
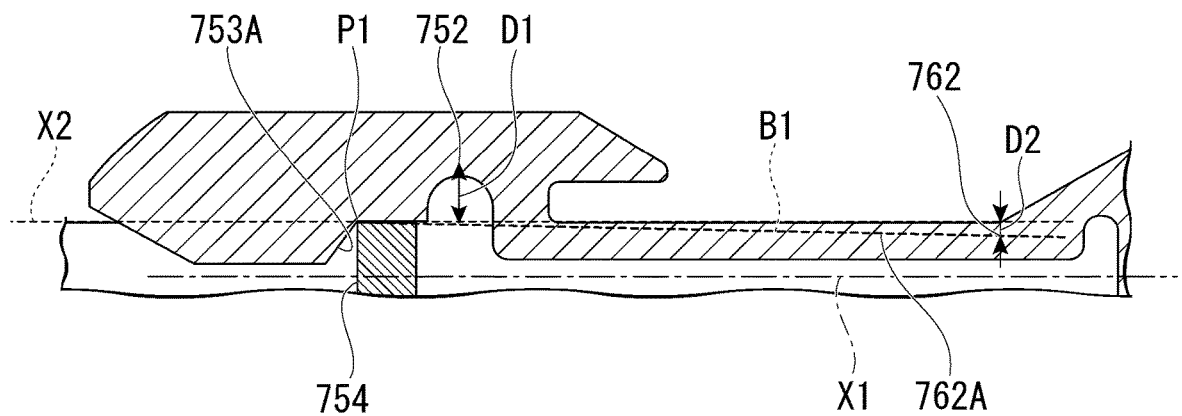
FIG. 14 is a view showing another example of a second deformation portion.

In the above described examples, the portion near the connection portion T in the plate-shaped portion 76 is regarded as the second deformation portion; however, the position of the second deformation portion is not limited thereto. In order to realize the above-mentioned operation for releasing the connection between the hook and the link, it only has to realize a positional relationship such that a moment larger than the moment generated in the second deformation portion by the traction force F is generated in the first deformation portion. In other words, as shown in FIG. 14, it only has to determine the position of the second deformation portion such that the distance D1 between the first deformation portion 752 and the line X2 that is parallel to the central axis X1 and passes through the contact portion P is longer than the distance D2 between the line X2 and the second deformation portion 762. For example, the portion 762A of the plate-shaped portion 76 located more distal than the connection site T may correspond to the second deformation portion. According to the present embodiment, since the plate-shaped portion extends substantially parallel to the central axis X1, any position of the plate-shaped portion may be considered as the second deformation portion.

The position of the first deformation portion in the central axis direction of the hook is not particularly limited as long as the first deformation portion is apart from the base line in the connection state. For example, the first deformation portion 752 may be provided at the distal end side of the hook more than the contact portion P.

Figure 15:
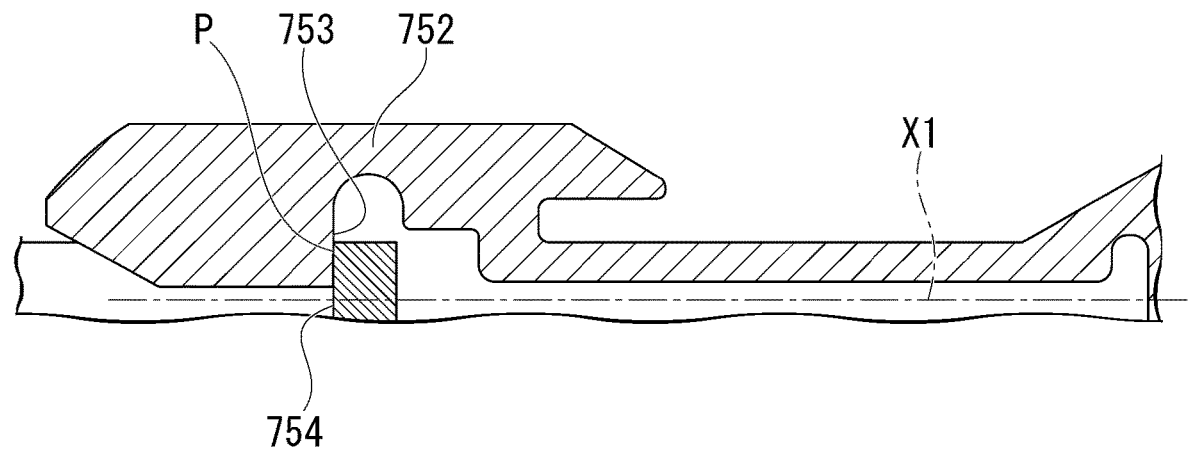
FIG. 15 is a partial enlarged view showing a modification of the hook.

In the modification shown in FIG. 15, the first deformation portion 752 is provided at a position closer to the contact portion P in the direction in which the central axis X1 extends than that according to the above embodiment (FIGS. 1 to 11). In this manner, the moment applying to the claw portion 75 increases, and the connection is released smoothly. In order to enhance this effect, it is preferable to make the first deformation portion 752 to be located at the same position as the contact portion P in the direction in which the central axis X1 extends.

Another exemplary embodiment of the present disclosure will be described with reference to FIGS. 16 to 19. In the following description, the same components which are already described will be designated by the same reference numerals and redundant description will be omitted.

Figure 16:
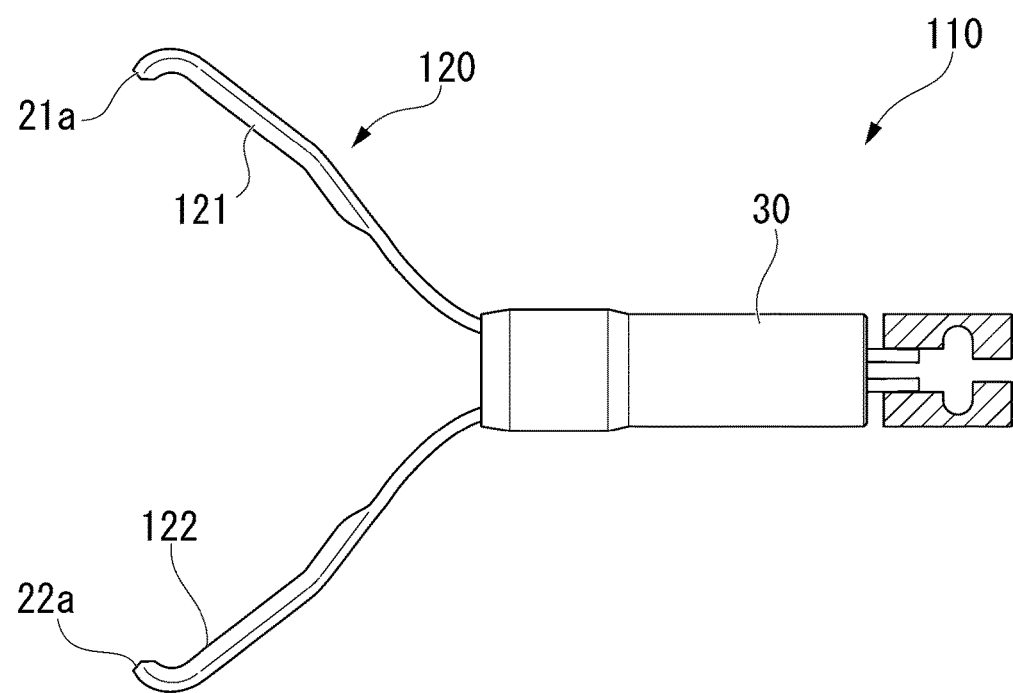
FIG. 16 is a view showing a clip unit according to an exemplary embodiment of the present disclosure.

FIG. 16 shows the clip unit 110 according to the present embodiment. The clip unit 110 includes an arm portion 120 and a pressing tube 30. The internal configuration of the pressing tube 30 is the same as that of the above embodiment (FIGS. 1 to 15).

Figure 17:
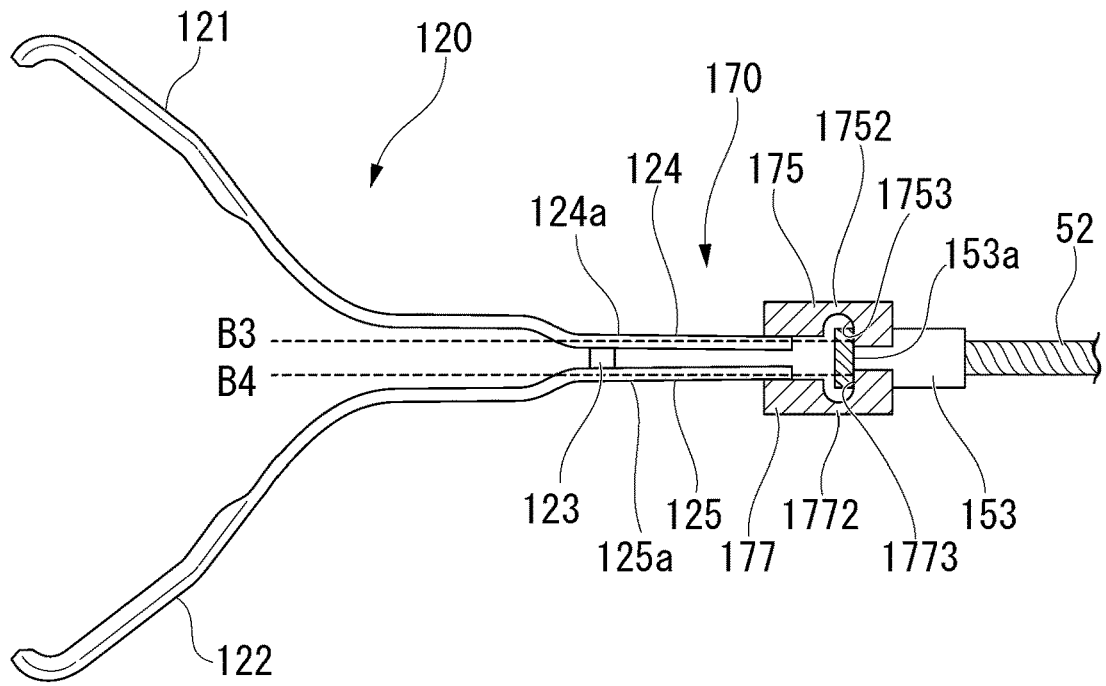
FIG. 17 is a view showing a connection structure between the hook and the base of the clip unit.

FIG. 17 shows a connection structure of the operation wire 52 and the arm part 120, that is, the configuration of a link according to the present embodiment. The first arm 121 and the second arm 122 are individual members and joined by a joint portion 123. The first arm 121 and the second arm 122 extend toward the rear side of the joint portion 123. Examples of the method for forming the joint portion 123 include welding, soldering, bonding, brazing or the like.

Claw members 175, 177 are attached to the proximal ends of the first arm 121 and the second arm 122, respectively. The claw member 175 has a first deformation portion 1752 and a hook surface 1753. The claw member 177 has a first deformation portion 1772 and a hook surface 1773.

The claw members 175, 177 may be formed of metal or the like, and may be formed of the same material as that of the first arm 121 and the second arm 122. The claw members 175, 177 may be fixed to the first arm 121 and the second arm 122 by welding, soldering, bonding, brazing, or the like.

A base 153 is fixed to the distal end of the operation wire 52. The shape of the base 153 is not particularly limited as long as the base surface 153a that is capable of being engaged with the hook surface 1753 and the hook surface 1773 is formed, and the base 153 may have the same shape as that of the base 20a.

According to the present embodiment, the operating wire 52 and the clip unit 110 are connected by the claw members 175, 177 sandwiching the base 153.

In the state shown in FIG. 17 in which the operation wire 52 and the arm portion 120 are connected, the portions proximal than the joint portion 123 of the first arm 121 and the second arm 122 function as the plate-shaped portions 124, 125, and the regions near the joint portion 123 in the plate-shaped portions 124, 125 function as the second deformation portions 124a, 125a, respectively.

The first deformation portion 1752 and the first deformation portion 1772 are at positions separated from the baseline B3 of the first arm 121 and the baseline B4 of the second arm 122, respectively.

That is, according to the present embodiment, the clip unit has the hook 170 at the proximal end portion of the arm portion 120, and the operation wire has the base.

Figure 18:
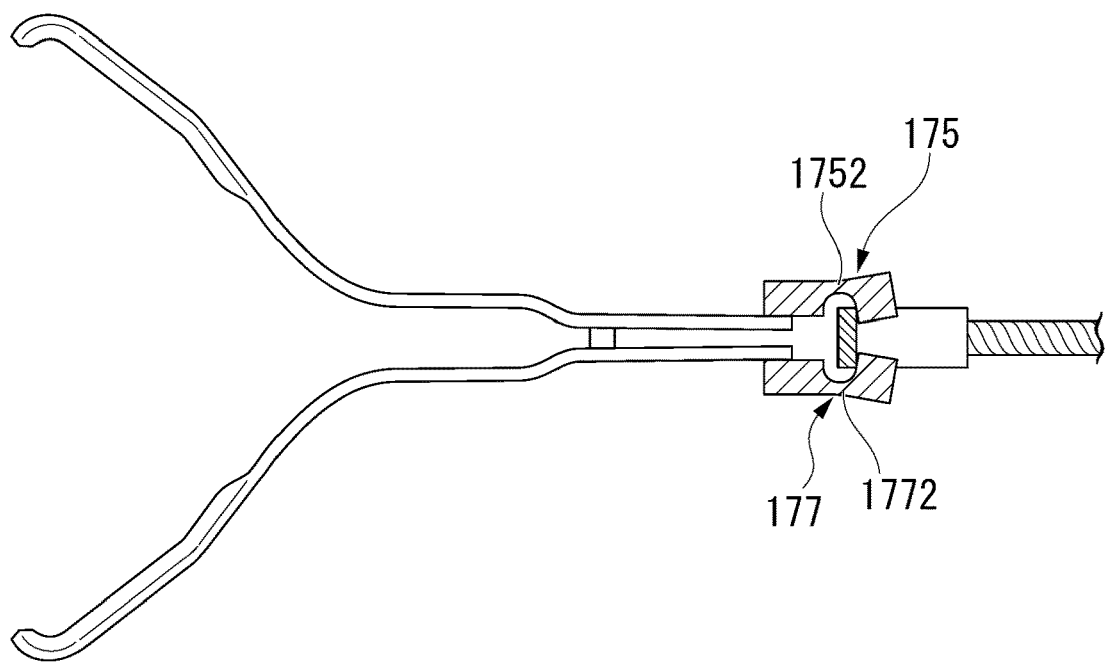
FIG. 18 is a view showing a process of releasing the connection between the hook and the base.
Figure 19:
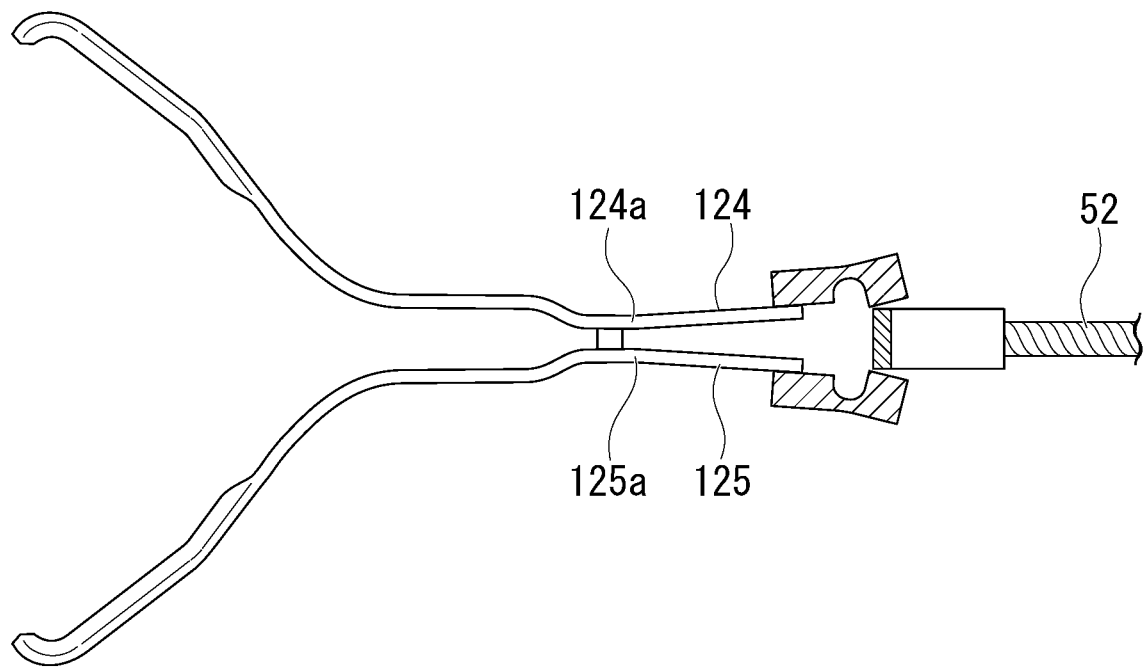
FIG. 19 is a view showing a process of releasing the connection between the hook and the base.

According to the present embodiment, after the arm of the clip unit is locked, as shown in FIG. 18, firstly, the rear portions of the claw members 175, 177 provided in the clip unit rotate around the first deformation portions 1752, 1772 as centers respectively. Subsequently, as shown in FIG. 19, the plate-shaped portions 124, 125 rotate around the second deformation portions 124a, 125a as centers, respectively, and the connection between the clip unit and the operation wire is released.

Similar to the above embodiment (FIGS. 1 to 15), the clip unit and the ligation device according to the present embodiment may achieve both goals of indwelling the clip unit in the body while clamping the hard tissue and making the operation to be easy.

According to the present embodiment, since the hook 170 is provided in the clip unit, the hook 170 is indwelled inside the body together with the clip unit 110. Accordingly, there is an advantage that the hook does not fatigue and fracture due to the repeatedly engagement and connections by applying the configuration to the reload type ligation device configured to attach a new clip to the applicator and then perform the indwelling operation again.

Another exemplary embodiment of the present disclosure will be described with reference to FIGS. 20 to 27. In the following description, the same components as those already described will be designated by the same reference numerals and redundant description will be omitted.

A ligation device 1C according to the present embodiment includes a clip unit (treatment portion) 210 and an applicator 50 configured to operate the clip unit 210.

Figure 20:
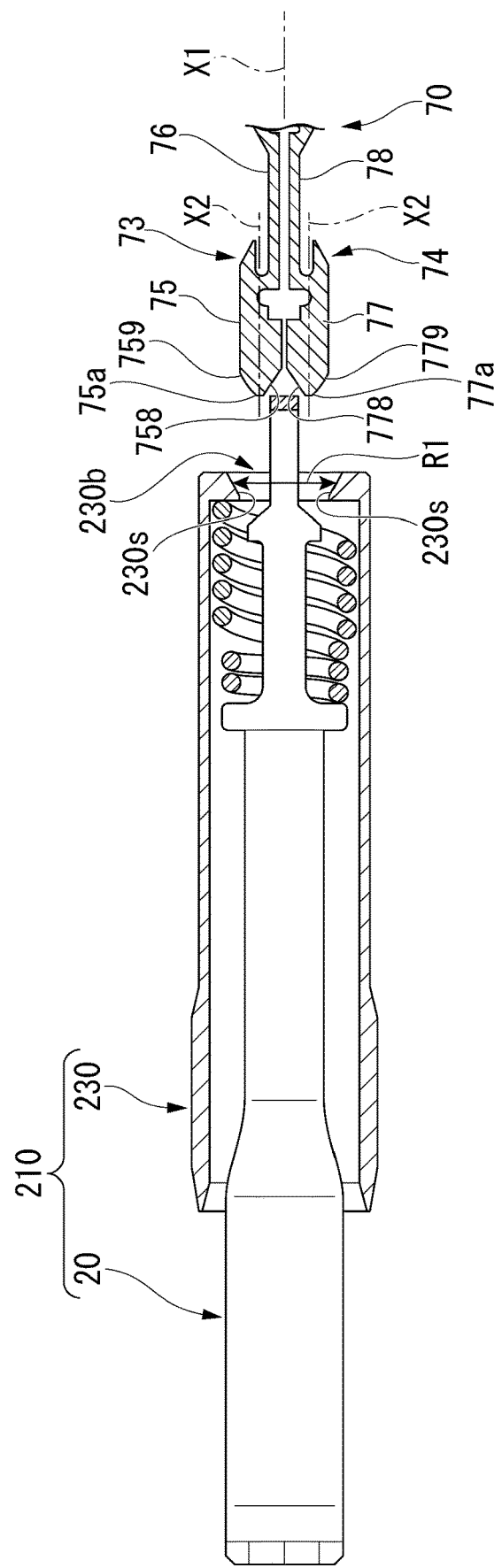
FIG. 20 is a view showing a clip unit of a ligation device according to an exemplary embodiment of the present disclosure.

FIG. 20 is a view showing the clip unit 210. The clip unit 210 includes the arm portion 20 and the pressing tube 230.

The pressing tube 230 is the same as the pressing tube 30 of the above embodiment (FIGS. 1 to 15) except for the shape of the proximal end opening 230b. As shown in FIG. 20, the proximal end opening 230b is formed in a tapered shape whose inner diameter R1 increases toward the outside (proximal end side) of the proximal end opening 230b. The tapered portion of the proximal end opening 230b is regarded as the engaged surface 230s.

The shape of the hook 70 will be described in more detail.

The distal end portion 75a of the claw portion 75 in the engagement arm 73 of the hook 70 is formed in a tapered shape whose dimension is decreased toward the distal end. As shown in FIG. 20, the distal end portion 75a is formed in a shape (for example, a tapered shape or an SR shape) whose thickness decreases toward the distal end.

The distal end portion 75a of the claw 75 has a first engagement surface 758 and a second engagement surface 759. As shown in FIG. 20, the first engagement surface 758 and the second engagement surface 759 are arranged on both sides of the axis X2 so as to sandwich the axis X2, wherein the axis X2 passes through the distal end of the engagement arm 73 and is parallel to the central axis X1.

The first engagement surface 758 is arranged on the central axis X1 side (inside) with respect to the axis X2. The normal line of the first engagement surface 758 is directed to the direction approaching the central axis line X1. The first engagement surface 758 may be a flat surface or a curved surface.

The second engagement surface 759 is arranged on the opposite side (outside) of the central axis X1 with respect to the axis X2. The normal line of the second engagement surface 759 is directed to the direction separated from the central axis line X1. The second engagement surface 759 may be a flat surface or a curved surface.

Similar to the claw portion 75, the claw portion 77 in the engaging arm 73 of the hook 70 is also formed in a tapered shape such that the dimension thereof decreases toward the distal end side. The distal end portion 77a of the claw 77 has a first engagement surface 778 and a second engagement surface 779, similar to the claw 75.

FIG. 21 to FIG. 24 are cross-sectional views of a connecting portion showing a process of connecting the clip unit 210 and the applicator 50. The operation of the ligation device 1C having the above-described configuration will be described. The user uses a cartridge 40 to connect the clip unit 210 and the applicator 50 before inserting the ligation device 1C into the endoscope.

Figure 21:
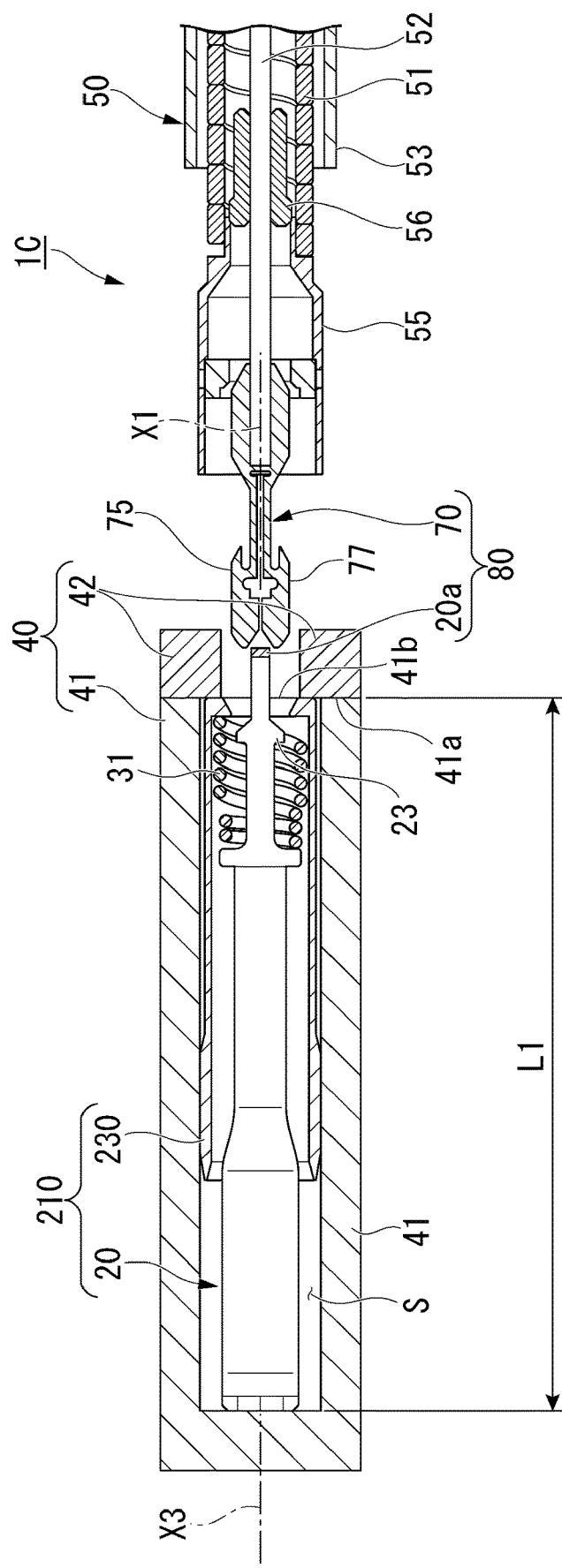
FIG. 21 is a partial cross-sectional view of the connection portion showing a process of connecting the clip unit and the applicator.

As shown in FIG. 21, the cartridge 40 is a substantially rectangular parallelepiped case configured to be capable of accommodating the clip unit 210. The cartridge 40 has a cartridge body 41 and a fastener 42.

The cartridge body 41 is formed in a bottomed cylindrical shape. As shown in FIG. 21, the cartridge body 41 has an internal space S for accommodating the clip unit 210 in a state in which the arm portion 20 is accommodated in the pressing tube 230 and the clip unit 210 is unlocked. The cartridge body 41 has an opening 41b communicating with the internal space S at one end portion 41a at the central axis X3 side of the internal space S.

In the internal space S of the cartridge body 41, the length L1 in the central axis X3 direction is shorter than the length of the arm portion 20 accommodated in the pressing tube 230 in the longitudinal axis direction as shown in FIG. 21. Therefore, at the time of accommodating the arm unit 20 in the state in which the arm portion 20 is accommodated in the pressing tube 230, the base 20a is arranged outside the cartridge body 41. The base 20a is arranged on the central axis line X3.

The fastener 42 is attached to the end portion 41a of the cartridge body 41 so as to be slidable in a direction orthogonal to the central axis X3. The fasteners 42 are arranged on both sides of the center of the opening 41b to sandwich the center of the opening 41 when viewed from the direction of the central axis X3. The fastener 42 may move to a first position to cover part of the opening 41b by being slid in the direction approaching the central axis X3. Furthermore, the fastener 42 may move to a second position so as to not to cover the opening 41b by being slid in the direction separating from the central axis X3.

The user moves the fastener 42 to the second position. The user accommodates the arm portion 20 in the pressing tube 230. The user accommodates the clip unit 210 in the state in which the arm portion 20 is accommodated in the pressing tube 230 and the clip unit 210 is unlocked in the internal space S of the cartridge body 41. Subsequently, the user moves the fastener 42 to the first position. As shown in FIG. 21, the distal end of the arm portion 20 comes in contact with the cartridge body 41. The proximal end of the pressing tube 230 comes in contact with the fastener 42 located at the first position. As a result, the arm portion 20 maintains the closed configuration in the state in which the arm portion 20 is not locked with respect to the pressing tube 230.

Figure 22:
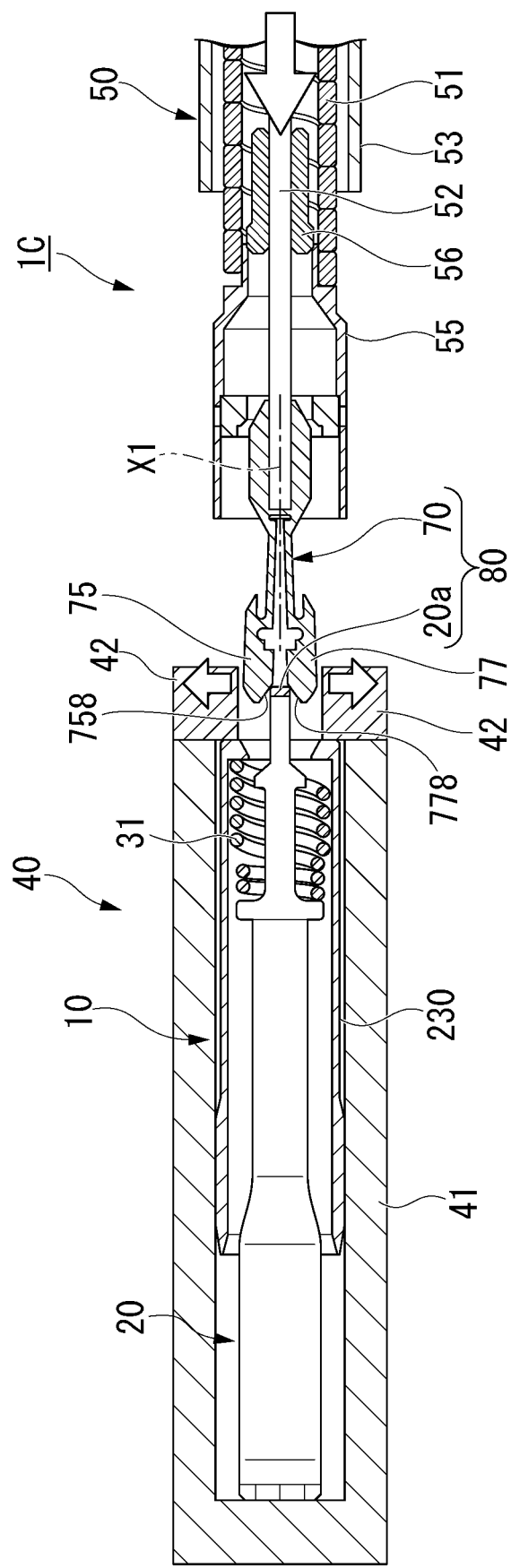
FIG. 22 is a partial cross-sectional view of the connection portion showing the process of connecting the clip unit and the applicator.

As shown in FIG. 22, the user moves the applicator 50 to approach the cartridge 40 accommodating the clip unit 210. The user makes them to approach each other in a state in which the base 20a is positioned on the central axis X1 of the hook 70. The base 20a and the first engagement surface 758 engage with each other. Since the normal line of the first engagement surface 758 is directed to the direction approaching the central axis X1, the claw portion 75 moves in the direction away from the central axis X1. The base 20a and the first engagement surface 778 engage with each other. Since the normal line of the first engagement surface 778 is directed in the direction approaching the central axis X1, the claw portion 77 moves in the direction away from the central axis X1.

Figure 23:
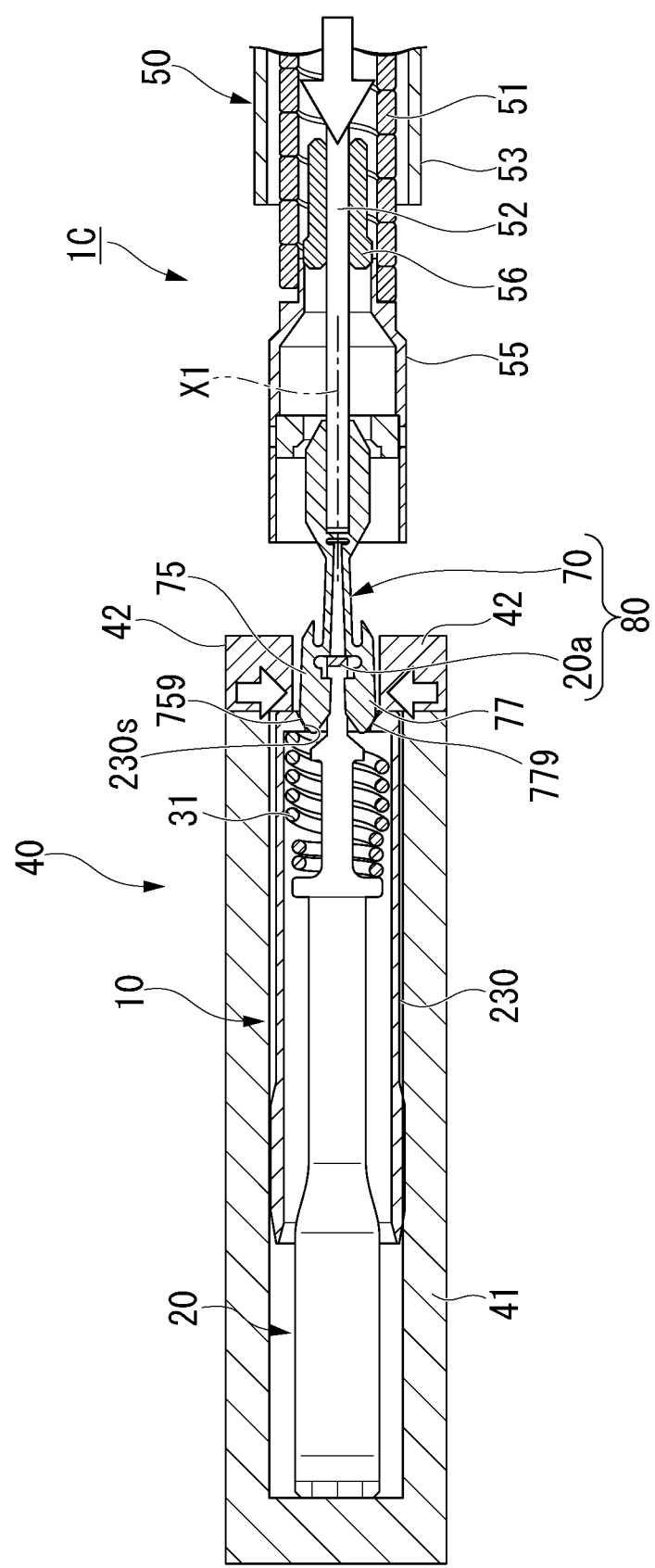
FIG. 23 is a partial cross-sectional view of the connection portion showing the process of connecting the clip unit and the applicator.

As shown in FIG. 23, the user further makes the applicator 50 to approach the cartridge 40. The engaged surface 230s of the pressing tube 230 and the second engagement surface 759 engage with each other. Since the normal line of the second engagement surface 759 is directed in the direction away from the central axis X1, the claw portion 75 moves in the direction approaching the central axis X1. The engaged surface 230s of the pressing tube 230 and the second engagement surface 779 are engaged with each other. Since the normal line of the second engagement surface 759 is directed in the direction away from the central axis X1, the claw 77 moves in the direction approaching the central axis X1.

The normal line of the engaged surface 230s is directed in the direction approaching the central axis X3. Therefore, as shown in FIG. 23, the claw portion 75 and the claw portion 77 engaged with the engaged surface 230s move in a direction approaching the central axis X3.

The user makes the applicator 50 to further approach the cartridge 40. As a result, as shown in FIG. 6, the locking surface (hook surface) 753 is locked to the front surface (base surface) 754 of the base 20a. The locking surface (hook surface) 773 is locked to the front surface (base surface) 754 of the base 20a. Due to the above-described operation, the clip unit 210 and the applicator 50 are connected.

Similar to the above embodiment, the clip unit 210 and the ligation device 1C according to the present embodiment may achieve both goals of indwelling the clip unit 210 in the state of clamping the hard tissue and making the operation to be easy. According to the present embodiment, it becomes easy to load the clip unit 210 into the applicator 50.

Figure 24:
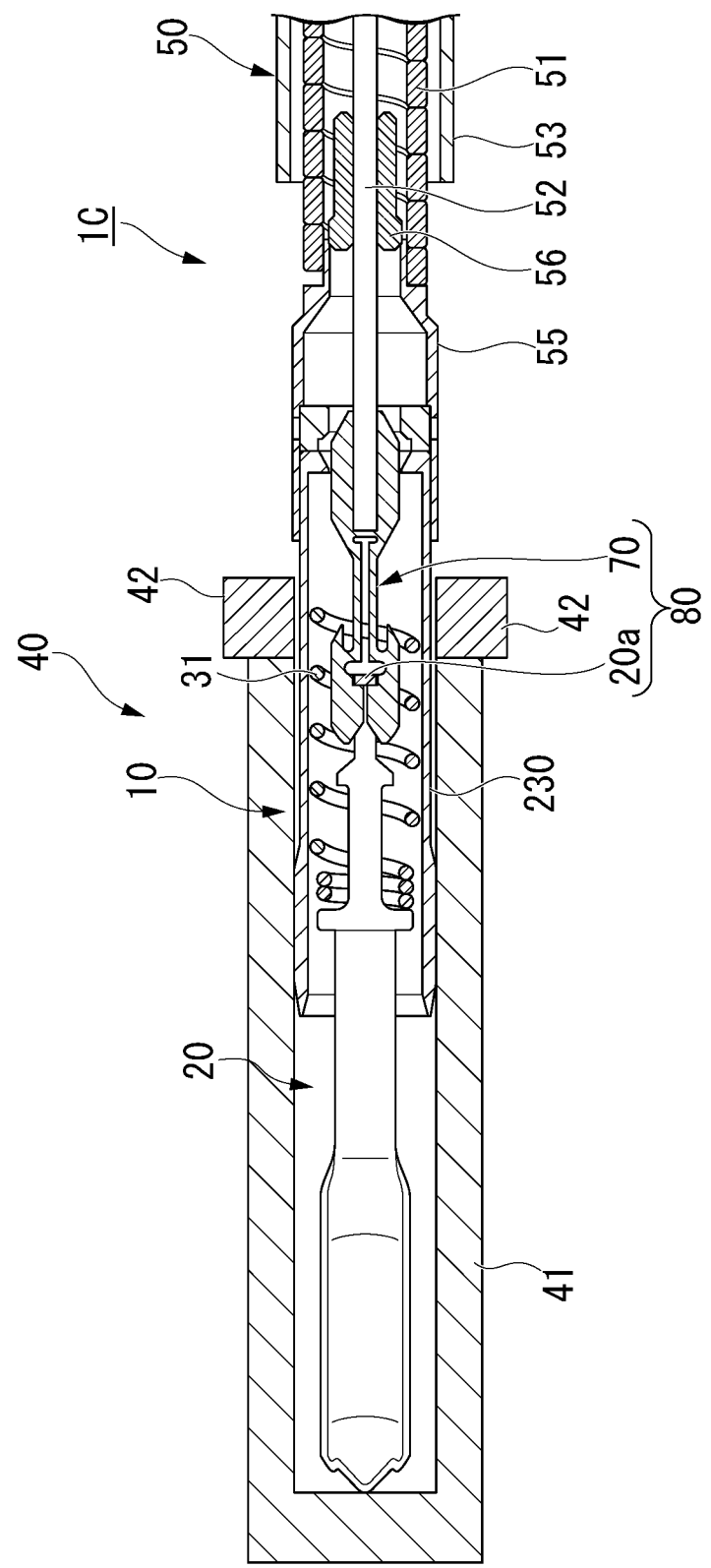
FIG. 24 is a partial cross-sectional view of the connection portion showing the process of connecting the clip unit and the applicator.

After the clip unit 210 and the applicator 50 are connected, the user moves the fastener 42 to the second position. As shown in FIG. 24, the elastic restoring force of the coil spring 31 causes the arm portion 20 to be transitioned to the open configuration. The proximal end of the pressing tube 230 moves to the outside of the cartridge body 41. The pressing tube 230 and the guide pipe 55 are connected. The connection between the clip unit 210 and the applicator 50 is maintained. Due to the above-described operation, the loading of the clip unit 210 to the applicator 50 is finished.

The user may separate the claw portion 75 and the claw portion 77 and move the claw portion 75 and the claw portion 77 to a position capable of clamping the base 20a by making the clip unit 210 and the applicator 50 to approach each other in the direction of connecting the clip unit 210 and the applicator 50. The user may further make the clip unit 210 and the applicator 50 to approach each other so as to make the claw portion 75 and the claw portion 77 to approach each other and move the claw portion 75 and the claw portion 77 to the position to be locked by the base 20a. The user may only make the clip unit 210 and the applicator 50 to approach each other in a direction of connecting the clip unit 210 and the applicator 50 so as to advance and retract the claw portion 75 and the claw portion 77 in the direction orthogonal to the connecting direction and easily connect the clip unit 210 and the applicator 50.

Modification 1

According to the present embodiment, an example in which the proximal end opening 230b of the pressing tube 230 is formed in a tapered shape is described; however, the fastener 42 of the cartridge 40 may be formed in a tapered shape instead of the proximal end opening 230b.

Figure 25:
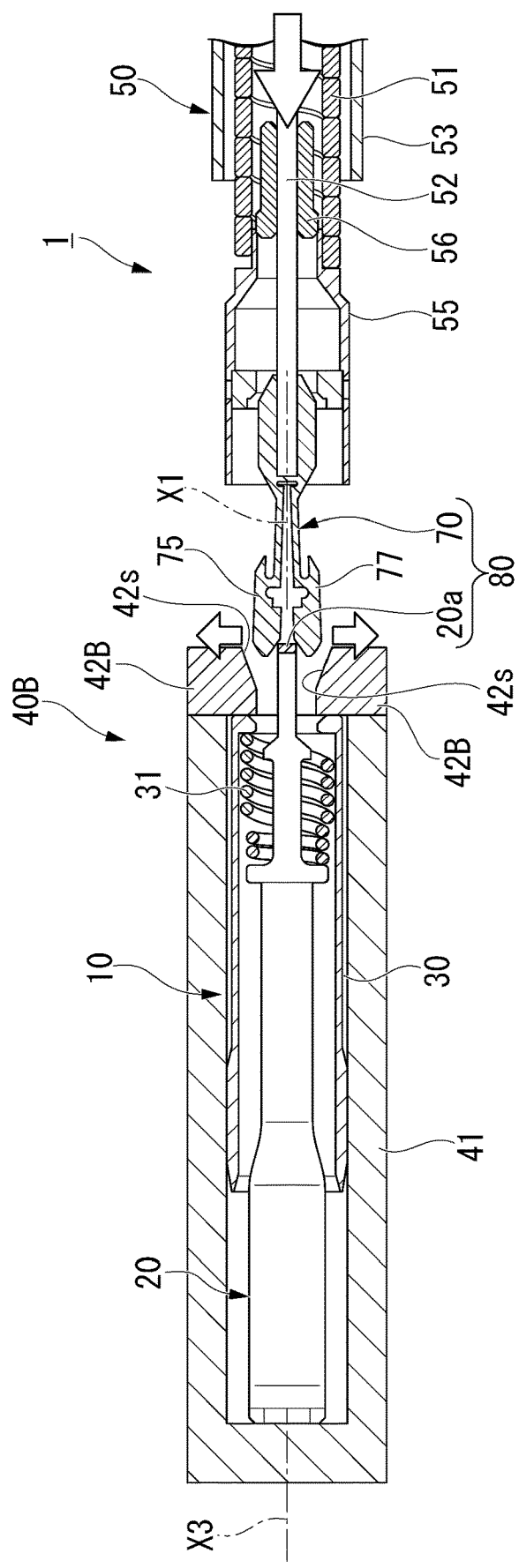
FIG. 25 is a partial cross-sectional view of the connection portion during a connection step using a cartridge having a modification of a fastener.
Figure 26:
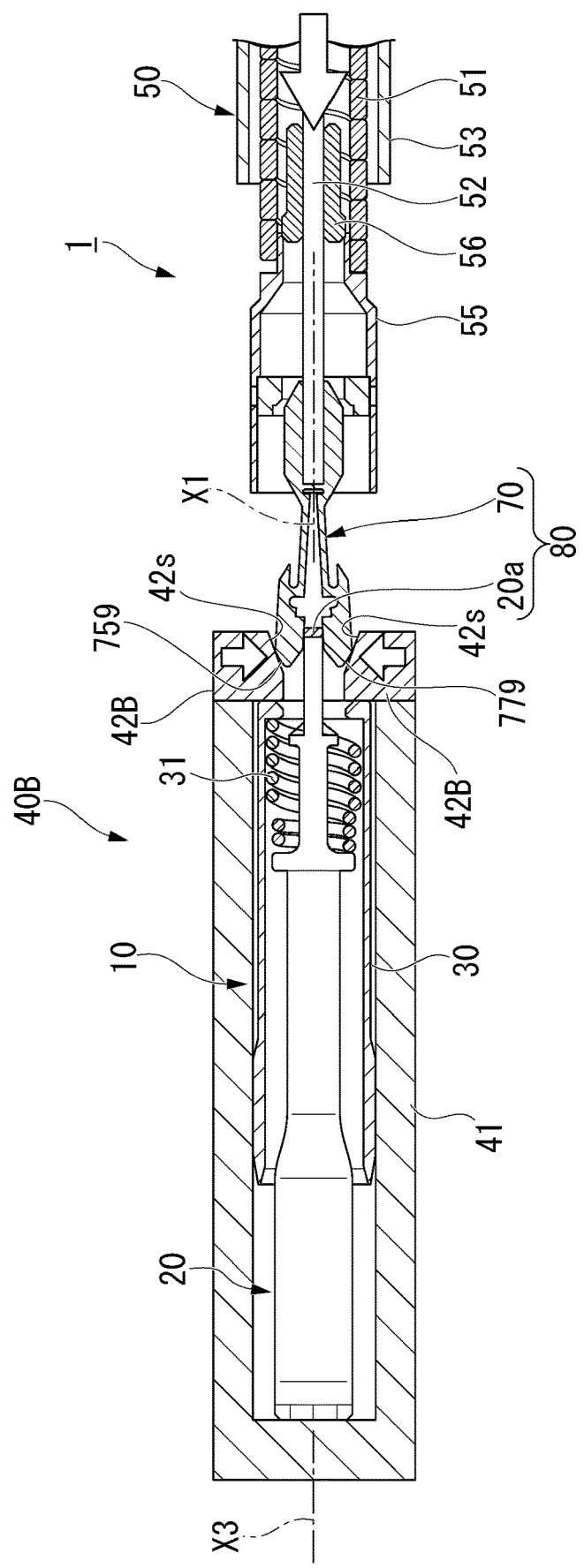
FIG. 26 is a partial cross-sectional view of the connection portion during the connection step using the cartridge having the modification of a fastener.
Figure 27:
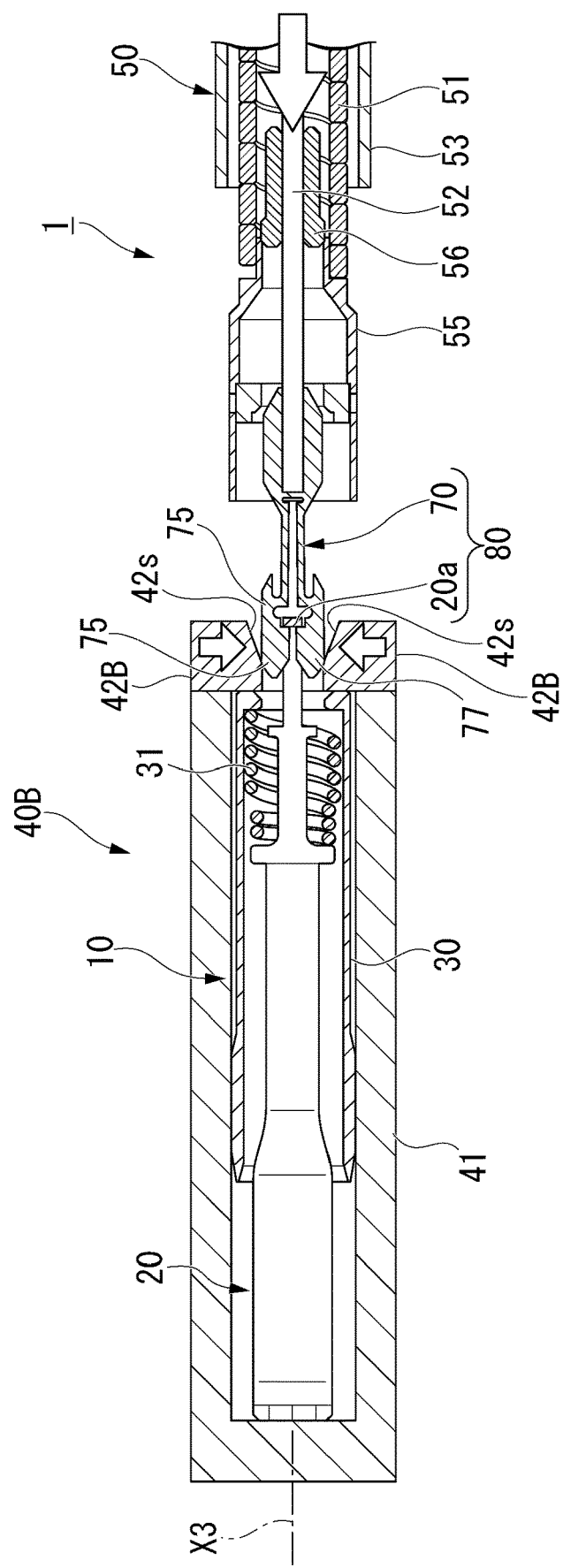
FIG. 27 is a partial cross-sectional view of the connection portion during the connection step using the cartridge having the modification of a fastener.

FIGS. 25 to 27 are cross-sectional views of a connection portion in a connection step using a cartridge 40B including a fastener 42B as a modification example of the fastener 42.

The fastener 42B is formed in a tapered shape at the central axis X3 side such that a distance to the central axis X3 increases toward the outside (proximal end side) of the cartridge 40B. The portion of the fastener 42B formed in the tapered shape is regarded as the engaged surface 42s.

As shown in FIG. 26, the user make the applicator 50 to further approach the cartridge 40B. The engaged surface 42s of the fastener 42B and the second engagement surface 759 engage with each other, and the claw portion 75 moves in a direction approaching the central axis X1 of the hook 70. The engaged surface 42s of the fastener 42B and the second engagement surface 779 are engaged with each other, and the claw portion 77 moves in the direction approaching the central axis X1 of the hook 70.

The normal line of the engaged surface 42s is directed in the direction approaching the central axis X3. Accordingly, as shown in FIG. 26, the claw portion 75 and the claw portion 77 engaged with the engaged surface 42s move in the direction approaching the central axis X3.

The user makes the applicator 50 to further approach the cartridge 40B. The claw portion 75 and the claw portion 77 further approach each other. As a result, as shown in FIG. 27, the claw portion 75 and the claw portion 77 are locked to the base 20a. By the above-described operations, the clip unit 10 and the applicator 50 are connected.

Modification 2

According to the present embodiment, the fastener 42 is attached to the end portion 41a of the cartridge body 41; however, the fastener 42 may be arranged in the internal space S of the cartridge body 41.

FIGS. 28 to 32 are cross-sectional views of a connection portion in a connecting step using a cartridge 40C including a fastener 42C as a modification of the fastener 42. In FIGS. 28 to 32, cross-sectional views of the connection portion by rotating at 90 degrees with respect to the central axis X3 of the internal space S are also shown. The cartridge 40C includes a cartridge body 41C and a fastener 42C.

As shown in FIG. 28, the fasteners 42C are arranged on both sides of the central axis line X3 to sandwich the central axis line X3 therebetween. The two fasteners 42C are arranged in the internal space S with the pressing tube 230 being sandwiched from both sides. The two fasteners 42C are arranged on both sides in the open-close direction P in which the arm portion 20 is opened and closed.

The fastener 42C has a fastener body 43, a first engagement protrusion 44, a second engagement protrusion 45, and a third engagement protrusion 46. The fastener body 43 is formed in a plate shape extending in the direction of the central axis X3.

The first engagement protrusion 44 is a convex portion that protrudes outwardly in the open-close direction P at the distal end of the fastener body 43. The distal end of the first engagement protrusion 44 is in contact with the inner circumferential surface 41s of the cartridge body 41C.

The second engagement protrusion 45 is a convex portion that protrudes outwardly in the open-close direction P at the proximal end of the fastener body 43. The distal end of the second engagement protrusion 45 is in contact with the inner circumferential surface 41s of the cartridge body 41C.

The third engagement protrusion 46 is a convex portion that protrudes inwardly in the open-close direction P at the proximal end of the fastener body 43. The distal end of the third engagement protrusion 46 engages with the proximal end of the pressing tube 230. The third engagement protrusions 46 of the two fasteners 42C are arranged at positions opposite to each other. The hook 70 may pass through the space between the third engagement protrusions 46.

The third engagement protrusion 46 has a third engagement surface 463 formed in a tapered shape on the distal end side. The normal line of the third engagement surface 463 is directed in the direction approaching the central axis line X3. The third engagement protrusion 46 has a fourth engagement surface 464 formed in a tapered shape on the base end side. The normal line of the fourth engagement surface 464 is directed in the direction approaching the central axis line X3. The fourth engagement surface 464 guides the distal end of the hook 70 inserted into the cartridge 40C in the direction approaching the central axis X3.

Similar to the cartridge body 41, the cartridge body 41C is formed in a bottomed cylindrical shape. As shown in FIG. 28, the cartridge body 41C has an internal space S capable of accommodating the clip unit 210 in the state in which the arm portion 20 is accommodated in the pressing tube 230 and the clip unit 210 is in the unlocked state. The cartridge body 41C has an opening 41b communicating with the internal space S at one end portion at the central axis X3 side of the internal space S.

As shown in FIG. 28, in the internal space S of the cartridge body 41C, the length L2 in the direction of the central axis X3 is sufficiently longer than the length of the arm portion 20 accommodated in the pressing tube 230 in the longitudinal axis direction.

The cartridge body 41C has an arm engagement recess 47, a first engagement recess 48, and a second engagement recess 49 in the internal space S. The arm engagement recess 47 is a concave portion into which the distal end side of the arm portion 20 is inserted. By inserting the arm portion 20 into the arm engaging recess 47, it is difficult for the arm portion 20 to be unstable with respect to the central axis X3.

The first engagement recess 48 is a concave portion that is recessed outwardly in the open-close direction P on the inner circumferential surface 41s of the cartridge body 41C. The first engagement recesses 48 are formed on both sides of the central axis line X3 to sandwich the central axis line X3 therebetween.

The second engagement recess 49 is a concave portion that is recessed outwardly in the open-close direction P on the inner circumferential surface 41s of the cartridge body 41C. The second engagement recesses 49 are formed on both sides of the central axis line X3 to sandwich the central axis line X3 therebetween.

The first engagement recess 48 is located on the distal end side more than the second engagement recess 49 in the direction of the central axis X3. The distance between the first engagement recess 48 and the second engagement recess 49 in the central axis X3 direction is substantially equal to the distance between the first engagement protrusion 44 and the second engagement protrusion 45 in the central axis X3 direction.

In the fastener 42C of the cartridge body 41C, in the initial state, the third engagement protrusion 46 that engages with the pressing tube 230 is pressed toward the proximal end side by the elastic restoring force of the coil spring 31. At this time, the first engagement protrusion 44 is positioned at the proximal end side more than the first engagement recess 48. In the initial state, the second engagement protrusion 45 is positioned at the proximal end side more than the second engagement recess 49.

The user makes the applicator 50 to approach the cartridge 40C in which the clip unit 210 is accommodated. As shown in FIG. 28, the hook 70 is inserted into the space between the two fasteners 40C. The distal end of the guide pipe 55 comes in contact with the proximal end of the fastener 42C.

Figure 29:
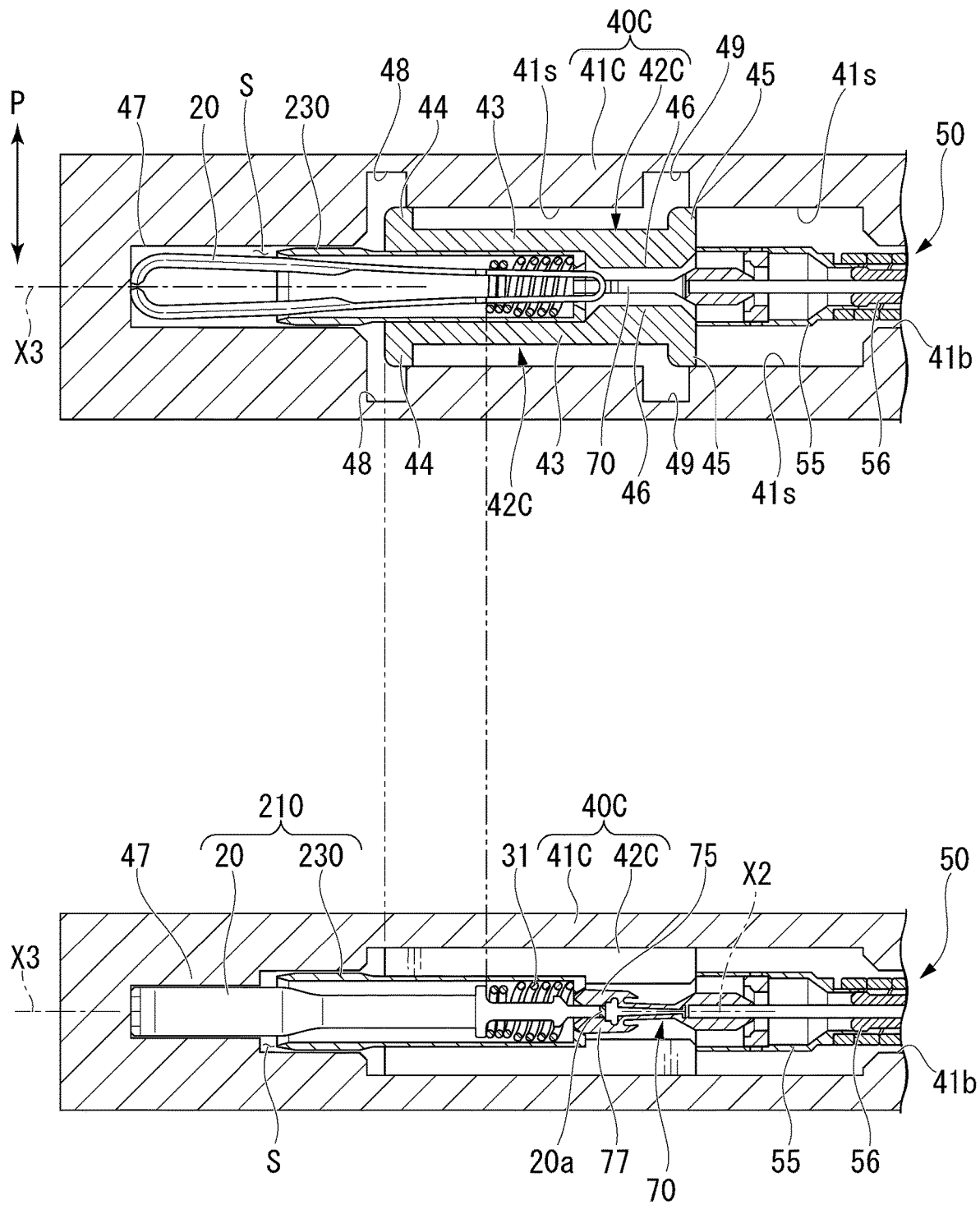
FIG. 29 is a partial cross-sectional view of a connection portion during a connection step using a cartridge having a further modification of a fastener.

As shown in FIG. 29, the user makes the applicator 50 to further approach the cartridge 40C. Similar to the present embodiment, the claw portion 75 and the claw portion 77 move in a direction away from the central axis X1. The distal end of the guide pipe 55 pushes the fastener 42C toward the distal end side with respect to the cartridge body 41C. The pressing tube 230 that engages with the third engagement protrusion 46 is pushed toward the distal end side with respect to the cartridge body 41C against the elastic restoring force of the coil spring 31.

As shown in FIG. 30, the user makes the applicator 50 to further approach the cartridge 40C, similar to the present embodiment, connects the clip unit 210 and the applicator 50. The fastener 42C that engages with the guide pipe 55 is further pushed toward the distal end side with respect to the cartridge body 41C. As shown in FIG. 30, when the clip unit 210 and the applicator 50 are arranged at a position where the clip unit 210 and the applicator 50 are connected to each other, the first engagement protrusion 44 is slightly located at the proximal end side than the first engagement recess 48. The second engagement protrusion 45 is slightly located at the proximal end side than the second engagement recess 49.

Figure 31:
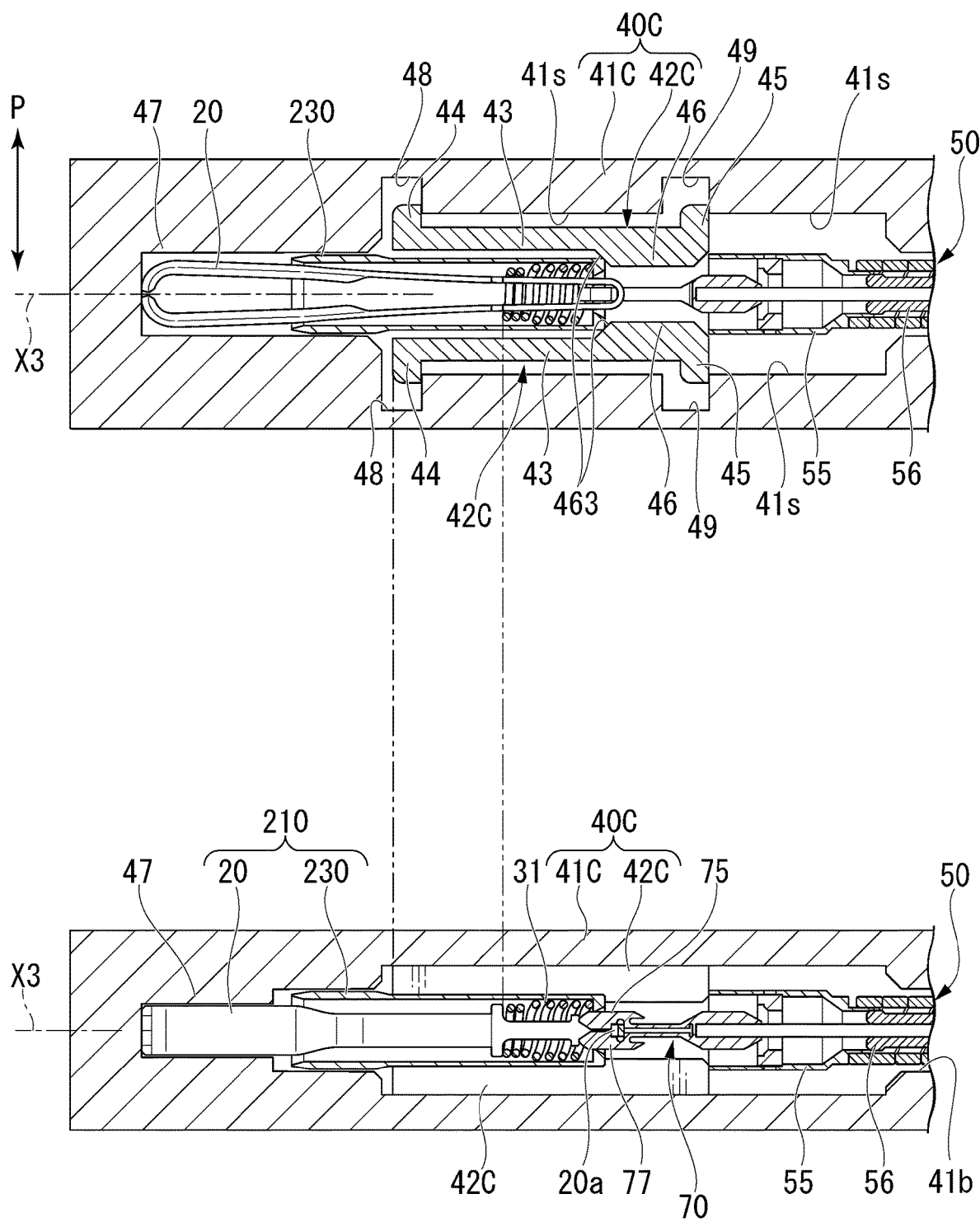
FIG. 31 is a partial cross-sectional view of a connection portion during a connection step using a cartridge having a further modification of a fastener.

As shown in FIG. 31, the user further pushes the applicator 50. As a result, the first engagement protrusion 44 and the second engagement protrusion 45 do not come into contact with the inner circumferential surface 41s of the cartridge body 41C. The proximal end of the pressing tube 230 pushes the third engagement surface 463 of the third engagement protrusion 46 toward the proximal end side by the elastic restoring force of the coil spring 31. Since the normal line of the third engagement surface 463 is directed in the direction approaching the central axis X3, the fastener 42C moves in a direction separating from the central axis X3.

As shown in FIG. 32, the fastener 42C moves in a direction separating from the central axis X3, and the first engagement protrusion 44 and the first engagement recess 48 engage with each other. The second engagement protrusion 45 and the second engagement recess 49 are engaged with each other.

As shown in FIG. 32, the pressing tube 230 that does not engage with the third engagement protrusion 46 moves to the proximal end side of the pressing tube 230 due to the elastic restoring force of the coil spring 31. As a result, the clip unit 210 moves to the opening 41b side.

In the cartridge 40C, it is not necessary for the user to open and close the fastener 42C. By making the clip unit 210 and the applicator 50 to approach each other only, the user may easily connect the clip unit 210 and the applicator 50, and take out the clip unit 210 after the connection from the cartridge 40C.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element.

In each of the above-described embodiments, an example in which the hook has a pair of engaging arms has been described; however, the aspect of the hook in the present disclosure is not limited thereto.

Figure 33:
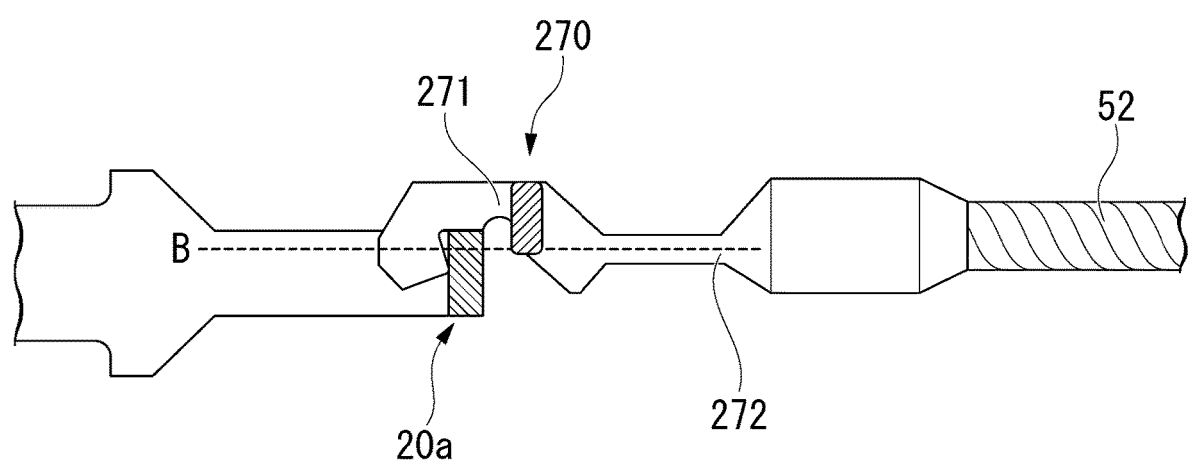
FIG. 33 is a view showing a link according to a modification of the present disclosure.

FIG. 33 shows an example of a hook including only one engagement arm. The hook 270 shown in FIG. 33 has one engagement arm 271. Even with such a configuration, by appropriately determining the positional relationship among the first deformation portion 271, the second deformable portion 272, the contact portion P, and the base line B while appropriately setting the bending rigidity of the first deformation portion 271 and the second deformable portion 272, it is possible to obtain the same effects as those according to the above-described embodiments.

In any of the above-described embodiments, the first deformation portion and the second deformation portion may be formed of different materials so as to achieve different bending rigidities of the first deformation portion and the second deformation portion. The first deformation portion and the second deformable portion may have a structure such as a hinge or the like with a rotating shaft.

Figure 34:
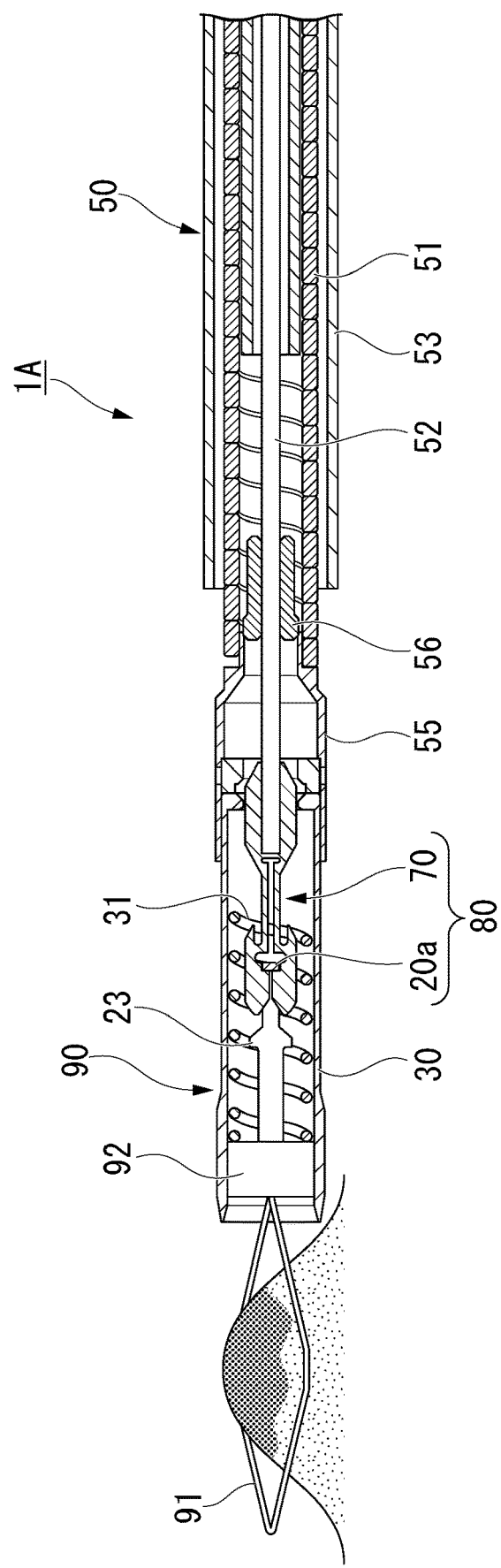
FIG. 34 is an enlarged cross-sectional view showing a distal end portion of a medical device according to a modification of the present disclosure.

The treatment portion according to the present disclosure is not limited to the above-mentioned clip unit. For example, similar to the medical device 1A shown in FIG. 34, the treatment portion 90 may have a snare loop 91 instead of the pair of arms.

In the treatment portion 90, the configuration inside the pressing tube 30 is substantially the same as that of the clip unit 10. A disk-shaped compression member 92 is attached between the locking portion 23 and the snare loop 91. When the operating wire 52 is retracted, the snare loop 91 is drawn into the pressing tube 30 and contracts, while the coil spring 31 is compressed by the compression member 92 such that the binding operation by the snare loop 91 may be repeated. When the locking portion 23 is moved to the outside of the pressing tube 30, the snare loop 91 is locked and in a small size. When the connection of the link 80 is released, the treatment portion 90 may be separated from the applicator 50.

According to the present modification, the loop shape of the snare loop 91 is not particularly limited.

Although the respective embodiments and modifications of the present disclosure have been described above, the technical scope of the present disclosure is not limited to the above-described embodiments, and configurations in the respective embodiments and modifications within the scope not departing from the spirit of the present disclosure. It is possible to change the combination of elements, make various changes to each configuration element, or delete each configuration element. For example, the configuration according to any one of above-described embodiments and modifications of the present disclosure may be appropriately combined with each modification of the operation section. The present disclosure is not limited by the above description, but only by the appended claims.

What is claimed is:

1. A medical device, comprising:
  a treatment portion including a clip or snare loop;
  an operation wire that extends along a longitudinal axis and is configured to operate the treatment portion; and
  a link configured to releasably connect the treatment portion and the operation wire, wherein the link comprises:
  a hook;
  a base configured to be releasably coupled to the hook;
  a first deformation portion disposed in the hook and configured to be deformed by movement of the operation wire in a proximal direction along the longitudinal axis of the operation wire; and
  a second deformation portion disposed in the hook and configured to be deformed to release the hook from the base by further movement of the operation wire in the proximal direction after the first deformation portion is deformed;
  wherein the first deformation portion is distal of the second deformation portion along the longitudinal axis of the operation wire, and a bending rigidity of the second deformation portion is smaller than a bending rigidity of the first deformation portion.

2. The medical device according to claim 1, wherein:
  the first deformation portion and the second deformation portion are configured to be deformed due to a force received from the operation wire,
  in a connection state in which the operation wire and the treatment portion are connected to each other, the first deformation portion is disposed at a position separated from a base line, and
  the base line is defined as an imaginary line running through the second deformation portion and a contact portion of the hook and the base in the connection state.

3. The medical device according to claim 2, wherein the first deformation portion is configured to be deformed such that the hook moves away from the base line in a separating direction, the separating direction being a direction along which the first deformation portion is separated from the base line in the connection state.

4. The medical device according to claim 2, wherein:
  the second deformation portion is: (i) disposed to be closer to the operation wire than the contact portion in a direction along the longitudinal axis of the operation wire, and (ii) separated from the longitudinal axis in a direction orthogonal to the longitudinal axis by a distance that is approximately equal to a distance between the contact portion and the longitudinal axis in the direction orthogonal to the longitudinal axis, and
  the first deformation portion is: (i) disposed at a position between the contact portion and the second deformation portion in the direction along the longitudinal axis, and (ii) separated from the longitudinal axis more than the second deformation portion in the direction orthogonal to the longitudinal axis.

5. The medical device according to claim 2, wherein a distance between the first deformation portion and the contact portion is shorter than a distance between the second deformation portion and the contact portion.

6. The medical device according to claim 2, wherein the hook is configured to move along the base line by an operation of the operation wire.

7. The medical device according to claim 2, wherein:
  the hook has a hook surface and the base has a base surface, and
  in the connection state, the base surface is in contact with the hook surface so as to be positioned between the hook surface and the second deformation portion.

8. The medical device according to claim 7, wherein:
  the hook includes two engagement arms that are symmetrically disposed with respect to a central axis of the hook, and
  each of the two engagement arms includes a respective first deformation portion, a respective second deformation portion, and a respective hook surface that is in contact with the base surface in the connection state.

9. The medical device according to claim 8, wherein:
- a distal end portion of at least one of the two engagement arms is tapered in a direction toward a distal end thereof,
- the distal end portion of the at least one of the two engagement arms includes a first engagement surface and a second engagement surface, and
- the first engagement surface and the second engagement surface are disposed at opposite sides of an axis so as to sandwich the axis, the axis passing through the distal end of the at least one of the two engagement arms and extending parallel to the central axis.

10. The medical device according to claim 9, wherein the first engagement surface is disposed in between the central axis and the axis, and the first engagement surface extends in a proximal direction so as to approach the central axis.

11. The medical device according to claim 9, wherein the axis is disposed in between the second engagement surface and the central axis, and the second engagement surface extends in a proximal direction so as to be inclined away from the central axis.

12. The medical device according to claim 2, wherein a distance between a central axis of the hook and the contact portion is longer than a distance between the central axis and the second deformation portion.

13. The medical device according to claim 2, wherein a distance between a central axis of the hook and the contact portion is shorter than a distance between the central axis and the second deformation portion.

14. The medical device according to claim 2, wherein the treatment portion includes the base and the operation wire includes the hook.

15. The medical device according to claim 2, wherein the treatment portion includes the hook and the operation wire includes the base.

* * * * *